US006472583B1

(12) United States Patent
Winn (10) Patent No.: US 6,472,583 B1
(45) Date of Patent: *Oct. 29, 2002

(54) PLASMID-BASED MUTATION DETECTION SYSTEM IN TRANSGENIC FISH

(75) Inventor: Richard N. Winn, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/427,218

(22) Filed: Oct. 26, 1999

Related U.S. Application Data (60) Provisional application No. 60/105,751, filed on Oct. 26, 1998.

(51) Int. Cl.$^7$ ...................... G01N 33/00; A01K 67/027; C12N 15/00

(52) U.S. Cl. ............................... 800/3; 800/20; 800/21; 800/25

(58) Field of Search ................ 800/20, 3, 21, 800/25

(56) References Cited

U.S. PATENT DOCUMENTS

| | | | |
|---|---|---|---|
| 5,347,075 A | 9/1994 | Sorge | 800/2 |
| 5,470,706 A | 11/1995 | Vijg et al. | 435/6 |
| 5,510,099 A | 4/1996 | Short et al. | 424/9.2 |
| 5,545,808 A | 8/1996 | Hew et al. | 800/2 |
| 5,589,155 A | 12/1996 | Sorge et al. | 424/9.2 |
| 5,602,300 A | 2/1997 | Gossen et al. | 800/2 |
| 5,817,290 A | 10/1998 | Vijg et al. | 424/9.2 |
| 5,824,287 A | 10/1998 | Sorge et al. | 424/9.2 |
| 6,114,600 A | 9/2000 | Ow et al. | 800/278 |
| 6,307,121 B1 * | 10/2001 | Winn | |

FOREIGN PATENT DOCUMENTS

| | | |
|---|---|---|
| EP | 0 289 121 B1 | 11/1988 |
| EP | 353 812 B1 | 1/1994 |
| JP | 2618973 | 1/1989 |
| JP | 96 029 093 B2 | 5/1990 |
| JP | 08 205708 | 8/1996 |
| NL | 8801826 | 2/1990 |
| NL | 9100567 | 11/1992 |
| WO | WO 91/15579 | 10/1991 |
| WO | WO 92/17605 | 10/1992 |
| WO | WO 93/15769 | 8/1993 |
| WO | WO 93/17123 | 9/1993 |
| WO | WO 97/05484 | 2/1997 |
| WO | WO 99/62333 | 12/1999 |
| WO | WO 00/24246 | 5/2000 |

OTHER PUBLICATIONS

Winn et. al. , Detection of mutations in transgenic fish carrying a bacteriophage transgene target, 2000; PNAS, vol. 97:12655–12660.*

Amanuma et al. Nature Genetics 18:62–65, 2000.*

Bayer et al., "A Transgene Containing IacZ is Expressed in Primary Sensory Neurons in Zebrafish," *Development*, 115:421–426 (1991).

Lin, et al., "IacZ Expression in Germline Transgenic Zebrafish Can Be Dectected in Living Embryos," *Developmental Biology*, 161:77–83 (1994).

Article: "Scientists fish for toxicity clues," *Chemistry & Industry*, pp. 131 (1999).

Fosgate, Ed., "Fish may soon replace lab mice," *UGA, School of Forrest Resources, Alumini Association Publication, Forresters' Log*, pp. 6 and 8 (1999).

Bearzotti et al., "Gene expression following transfection of fish cells," *Journal of Biotechnology*, 26:318–325 (1992).

Detrick, "Transgenic Fish Model for Mutagenicity Testing," *Crisp Data Base National Institute of Health*, located at website: alt1.csa.com/htbin/ids51/procskel.cgi, Abstract, 1 page (1994).

Fosgate, "Transgenic fish may give lab mice day off," *Georgia Magazine*, p. 11 (1999).

Susman, "Gene–altered fish check new chemicals," located at website: news.chemicalonline.com/wires/19990124–421734772.htm, 2 pages. (1999).

Torassa, "Animals Hold Key to Cures," located at website: abcnews.go.coM:80/sections/science/DailyNews/scorpions9990125.htm, 2 pages. (1999).

"MutaPlax™ Transgenic Lambda DNA Packaging System," [online] [retrieved May 7, 1998]. Retrieved from the Internet: interscience.com/epicentre/mutplxc2.html, 1 page. 1998.

"MutaPlax cII–Select™ Packaging and Selection Kit," [online][retrieved May 28, 1998]. Retrieved from the Internet: interscience.com/epicentre/multiplxc2.html, 1 page. 1998.

"A short description of the lambda cII system," [online]. Biology Dept., University of Victoria, Canada, [retrieved on May 8, 1998]. Retrieved from the Internet: darwin.ceh.uvic.ca/bigblue/cci–info.htm, 1 page. 1998.

"A short description of the Big Blue system," [online]. Biology Dept., University of Victoria, Canada, [retrieved on May 28, 1998]. Retrieved from the Internet: <URL:http://darwin.ceh.uvic.ca/bigblue/bbinfo.htm>, 1 page. 1998.

"A short description of the lambda cII system," [online]. Biology Dept., University of Victoria, Canada, [retrieved on May 8, 1998]. Retrieved from the Internet: <URL:http://darwin.ceh.uvic.ca/bigblue/cci–info.htm>, 1 page. 1998.

(List continued on next page.)

*Primary Examiner*—Dave T. Nguyen
*Assistant Examiner*—Ram R. Shukla
(74) *Attorney, Agent, or Firm*—Mueting, Raasch & Gebhardt, P.A.

(57) ABSTRACT

The present invention provides transgenic fish whose somatic and germ cells contain a genomically integrated plasmid containing a heterologous mutation target nucleic acid sequence that is detectable via bioassay in a bacterial cell into which the target nucleic acid has been introduced. The frequency and character of mutations in the mutatable target nucleic acid sequence following exposure of the transgenic fish to one or more potentially mutagenic agents can thus be evaluated.

32 Claims, 1 Drawing Sheet

OTHER PUBLICATIONS

Barnes, "Fish Embryonal Stem Cells for Development of Transgenics," Grant No. 5 R01 ES 06011–06 [online] Oregon State University [retrieved Mar. 24, 1998]. Retrieved from the Internet: <URL:http://cos.gdb.org/cgi/bin/open/feddb/NIH/nih/81168666/81171512/data3/work/db–annex/nih/nih.data/seed=fish+transgenic+ak at cos.gdb.org>, 1 page. 1998.

"Big Blue® λLIZ Shuttle Vector," [online]. Strategene [retrieved May 28, 1998]. Retrieved from the Internet: <URL:http://www.stratagene.com/vol10_3/figures/p100–101–fl.htm>, 1 page. 1998.

Burkhart et al., "Non–Mammalian and Environmental Sentinels in Human Health: "Back to the Future?"," *Human and Ecological Risk Assessment*, 3(3):309–328 (1997).

Burkhart et al., "Spontaneous and Induced Mutagenesis in Transgenic Animals Containing ΦX174," Abstract, *Environmental and Molecular Mutagenesis*, 21(22):9 (1993).

Burkhart, "Comparative Mutagenesis in Aquatic Models, Rodents, and Cells in Culture," Abstract, Grant No. Z01 ES21187–02 [online]. NIH Intramural [retrieved Mar. 24, 1998]. Retrieved from the Internet: <URL:http://cos.gdb.org/cgi–bin/open/feddb/NIH/nih/183654826/183657932/data3/work/db–annex/nih/nih.data/seed=fish+transgenic+ak at cos.gdb.org>, 1 page. 1998.

Chen, "Transgenic Fish as a Model for Environmental Toxicology," Abstract, Grant No. 5 R01 RR11680–03 [online]. University of Connecticut STORRS [retrieved Mar. 24, 1998]. Retrieved from Internet <URL:http://cos.gdb.org/cgi–bin/open/feddb/NIH/nih/177554210/17558224/data3/work/db–annex/nih/nih.data/seed=fish+transgenic+ak at cos.gdb.org>, 1 page. 1998.

Dycaico et al., "The use of shuttle vectors for mutation analysis in transgenic mice and rats," *Mutation Research*, 307(2):461–478 (1994).

Epicentre Technologies, "cII Primer" Product Information, Catalog #P67PL1, and #P67PL2, 1 page (1996).

Gallagher et al., "A Comparative Approach to 7,12–Dimethylbenz[A]Anthracene Effects: Metabolism and Mutagenesis in Mice and Fish," Abstract, *Environment and Molecular Mutagenesis*, 29(28):16 (1997).

Grunwald, "Embryo Stem Cell Cultures and Gene Transfer in Zebrafish," Abstract, Grant No. 5 R01 RR10253–04 [online]. University of Utah [retrieved Mar. 24, 1998]. Retrieved fom the Internet: <URL:http://cos.gdb.org/cgi-bin/open/feddb/NIH/nih/176701197/176704983/data3/work/db–annex/nih/nih.data/seed=fish+transgenic+ak at cos.gdb.org>, 1 page. 1998.

Gu et al., "Development of λ–based complementation assay for the preliminary localization of lacI mutants from the Big Blue™ mouse: implications for a DNA–sequencing strategy," *Mutation Research*, 307(2):533–540 (1994).

Guyomard et al.; "Integration and germ line transmission of foreign genes microinjected into fertilized trout eggs," *Biochimie*, 71(7):857–863 (1989).

Houdebine et al., "Transgenesis in fish," *Experientia*, 47(9);891–897 (1991).

International Agency for Research on Cancer (IARC), IARC Monographs on the Evaluation of Carcinogenic Risk of Chemicals to Humans, 7, IARC, Lyon., 253–260 (1974).

Kaiser et al., "Fishing for Toxic Chemicals," *Science*, 283(5403):775, 777 (Feb. 5, 1999).

Kohler et al., "Spectra of spontaneous and mutagen–induced mutations in the lacI gene in transgenic mice," *Proc. Natl. Acad. Sci. USA*, 88(18):7958–7962 (1991).

"λSelect–CII™Mutation Detection Sytem for Big Blue® Rodents," Instruction Manual, Stratagene, Catalog #720120, Revision #028001, pp. 1–21 (1998).

Liu et al., "Development of Expression Vectors for Transgenic Fish," *Biotechnology*, 8(12):1268–1272 (1990).

Lubzens et al., "Cryopreservation as a Tool in Aquaculture," Abstract only, *Israeli Journal of Aquaculture*, 44(4):137 (1992).

Murray et al., eds., *Transgenic Animals in Agriculture*, CABI Publishing, New York, Title page, publication page, and pp. 33, 88–89, 91, 93–95, 217–218, and 224–229 (1999).

"MutaPlax™ Transgenic Lambda DNA Packaging System." [online][retrieved May 7, 1998]. Retrieved from the Internet: <URL:http://www.interscience.com/epicentre/mutplxc2.html>, 1 page. 1998.

"MutaPlax cII–Select™ Packaging and Selection Kit," [online][retrieved May 28, 1998]. Retrieved from the Internet: <URL:http://www.interscience.com/epicentre/mutplxc2.html>, 1 page. 1998.

Nebert, "Transgenic Zebrafish–Sentinel for Aquatic Pollution", Abstract, Grant No. 5 R01 ES07058–02 [online]. University of Cincinnati [retrieved Mar. 24, 1998]. Retrieved from the Internet: <URL:http://cos.gdb.org.cgi-bin/open/feddb/NIH/nih/81969991/81973169/data3/work/db–annex/nih/nih.data/seed=fish+transgenic+ak at cos.gdb.org>, 1 page. 1998.

Provost et al., "Transgenic systems for in vivo mutation analysis," *Mutation Research*, 288(1):133–149 (1993).

Rokkones et al., "Microinjection and expression of a mouse metallothionein human growth hormone fusion gene in fertilized salmonid eggs," *Journal of Comparative Physiology B*, 158(6):751–758 (1989).

Sambrook et al., "Preparation of Reagents and Buffers Used in Molecular Cloning," *Molecular Cloning* 2nd Ed., Cold Spring Harbor Press, p.B.13 (1989).

Schwarz et al., "Nucleotide sequence of cro, cII and part of the O gene in phage λ DNA," *Nature*, 272(5652):410–414 (1978).

Shimada et al., "Some Characteristics of Radiation–or Enu–induced Mutations at the b Locus of the Medaka, Oryzias Latipes," Abstract GE 3, *Physiology, Genetics*, 7(6):1053 (1990).

Shimada et al., "Further Characterization of Radiation–or Enu–induced Mutations at the b Locus of the Medaka, Oryzias Latipes," Abstract, *Genetics* 8(6):1127 (1991).

Skopek et al., "Relative Sensitivity of the Endogenous hprt Gene and lacI Transgene in ENU–Treated Big Blue™ B6C3F1 Mice," *Environmental and Molecular Mutagenesis*, 26(1):9–15 (1995).

Strategene, *Big Blue™ Transgenic Mouse Mutagenesis Assay System*, Instruction Manual, La Jolla, CA, Title Page and table of contents only, 2 pages. (1992).

Stratagene Online, "Technical Information—Frequently Asked Questions—Big Blue®," [online]. Strategene [retrieved Mar. 24, 1998]. Retrieved from the Internet: <URL:http://www.stratagene.com/tech_ref/big_blue/faq.htm>, 3 pages. 1998.

Strategene Online, "Strategies Newsletters—A Positive Selection Assay for Mutation Analysis in Big Blue® Animals," [online]. Strategene [retrieved May 28, 1998]. Retrieved from the Internet: <URL:http://www.stratagene.com/vol10_3/p100–101.html>, 2 pages. 1998.

Winn, "Transgenic Fish Model for Mutation Detection," Grant No. 1 R24 RR11733–01A1 [online]. University of Georgia [retrieved Mar. 24, 1998]. Retrieved from the Internet: <URL:http://cos.gdb.org/cgi–bin/open/feddb/NIH/nih/177576697/177580360/data3/work/db–annex/nih/nih-.data/seed=fish+lambda+ak at cos.gdb.org 1 page. 1998.

Bailey et al., "Initiation, Promotion, and Inhibition of Carcinogenesis in Rainbow Trout," *Environ. Health Perspect.,* 71:147–153 (1987).

Black, "Aquatic Animal Neoplasia as an Indicator for Carcinogenic Hazards to Man," *Hazard Assessment of Chemicals: Current Developments,* vol. 3, Saxena, ed., Academic Press, New York, Title page, publication page, table of contents and pp. 181–232 (1984).

Boerrigter et al., "Plasmid–based transgenic mouse model for studying in vivo mutations," *Nature,* 377(6550):657–659 (1995).

Boerrigter et al., "Sources of Variability in Mutant Frequency Determinations in Different Organs of lacZ Plasmid–based Transgenic Mice: Experimental Features and Statistical Analysis," *Env. Mol. Mutagenesis,* 29(3):221–229 (1997).

Boerrigter et al., "High Sensitivity for Color Mutants in lacZ Plasmid–Based Transgenic Mice, as Detected by Positive Selection," *Env. Mol. Mutagenesis,* 32(2):148–154 (1998).

Burkhart et al., ENU–induced mutagenesis at a single A:T base pair in transgenic mice containing ΦX174 *Mutation Res.,* 292:69–81 (1993).

Culp et al., "High–frequency germ–line transmission of plasmid DNA sequences injected into fertilized zebrafish eggs," *Proc. Natl. Acad. Sci. USA,* 88(18):7953–7957 (1991).

Doll´´ et al., "Evaluation of a plasmid–based transgenic mouse model for detecting in vivo mutations," *Mutagenesis,* 11(1):111–118 (1996).

Douglas et al., "Sequence spectra of spontaneous lacZ gene mutations in transgenic mouse somatic and germline tissues", *Mutagenesis,* 9(5):451–458 (1994).

Driever et al., "Zebrafish: genetic tools for studying vertebrate development," *Trends Genet.,* 10(5):152–159 (1994).

Driever et al., "A genetic screen for mutations affecting embryogenesis in zebrafish," *Development,* 123:37–46 (1996).

DuBridge et al., "Recombinant shuttle vectors for the study of mutation in mammalian cells," *Mutagenesis,* 3(1):1–9 (1988).

Dycaico et al., "The use of shuttle vectors for mutation analysis in transgenic mice and rats," *Mutation Res.,* 307:461–478 (1994).

Goldsworthy et al., "Transgenic Animals in Toxicology," *Fund Appl. Toxicol.,* 22:8–19 (1994).

Gossen et al., "Efficient rescue of integrated shuttle vectors from transgenic mice: A model for studying mutations in vivo," *Proc. Natl. Acad. Sci.,* 86:7971–7975 (1989).

Gossen et al., "Plasmid Rescue form Transgenic Mouse DNA Using LacI Repressor Protein Conjugated to Magnetic Beads," *BioTechniques,* 14(4):624–629 (1993).

Gossen et al., "Spontaneous and X–ray induced deletion mutations in a LacZ plasmid–based transgenic mouse model," *Mut. Res.,* 331:89–97 (1995).

Hawkins et al., "Chapter 14: Carcinogenicity Tests Using Aquarium Fish," *Fundamentals of Aquatic Toxicology: Effects, Environmental Rate, and Risk Assessment,* Rand, ed., Taylor and Francis, pp. 421–446 (1995).

Hendricks, "Chemical Carcinogenesis in Fish," *Aquatic Toxicology,* Weber, ed., Raven Press, NY, pp. 149–211 (1982).

Hinton et al., "Cytological changes during progression of neoplasia in selected fish species," *Aquat. Toxicol.,* 11:77–112 (1988).

Inoue et al., "Stage–dependent expression of the chicken δ–crystallin gene in transgenic fish embryos," *Cell Differ. Dev.,* 27:57–68 (1989).

Inoue et al., "Electroporation as a new technique for producing transgenic fish," *Cell Differ. Dev.,* 29(2):123–128 (1990).

International Agency for Research on Cancer (IARC), World Health Organization, "Some anti–thyroid and related substances, nitrofurans and industrial chemicals," *IARC Monographs on the Evaluation of the Carcinogenic Risk of Chemicals to Man,* meeting of the IARC working groups, Lyon, Feb. 4–11 and Jun. 18–24, 1974, pp. 253–260 (1974).

Ishikawa et al., "Importance of Hepatic Neoplasms in Lower Vertebrate Animals as a Tool in Cancer Research," *J. Toxicol. Environ. Health,* 5(2–3):537–550 (1979).

Ishikawa et al., "Usefulness of the Medaka, *Oryzias latipes,* as a Test Animal: DNA Repair Processes in Medaka Exposed to Carcinogens," *Use of Small Fish Species in Carcinogenicity Testing, Natl. Cancer Inst. Monograph 65,* U.S. Dept. of Health and Human Services, National Institutes of Health, pp. 35–43 (1984).

Jakubczak et al., "Analysis of genetic instability during mammary tumor progression using a novel selection–based assay for in vivo mutations in a bacteriophage λ transgene target," *Proc. Natl. Acad. Sci. USA,* 93(17):9073–9078 (1996).

Lebkowski et al., "The lacI shuttle: Rapid analysis of the mutagenic specificity of ultraviolet light in human cells," *Proc. Natl. Acad. Sci. USA,* 82:8606–8610 (1985).

Lewis et al., "The Nature of Spontaneous and Induced Electrophoretically Detected Mutations in the Mouse," *Prog. Clin. Biol. Res.,* 209B:359–365 (1986).

Lu et al., "Integration: expression, and germ–like transmission of foreign growth hormone genes in medaka (*Oryzias latipes*)," *Mol. Mar. Biol. Biotechnol.,* 1(⅘):366–375 (1992).

Lu et al., "Pantropic retroviral vector integration, expression, and germline transmission in medaka (*Oryzias latipes*)," *Mol. Mar. Biol. Biotechnol.,* 6(4):289–295 (1997).

Malling et al. ,"Use of ΦX 174 as a shuttle vector for the study of in vivo mammalian mutagenesis," *Mutation Res.,* 212:11–21 (1989).

Masahito et al., "Fish Tumors and their Importance in Cancer Research," *Jpn. J. Cancer Res.,* 79(5):545–555 (1988).

Metcalfe, "Tests for Predicting Carcinogenicity in Fish," *CRC Rev. Aquat. Sci.,* 1(1):111–129 (1989).

Mirsalis et al., "Induction of hepatic mutations in lacI transgenic mice," *Mutagenesis,* 8:265–271 (1993).

Mirsalis et al., "Transgenic Animal Models for Detection of In Vivo Mutations," *Ann. Rev. Pharmacol. Toxicol.,* 35:145–164 (1995).

Müller et al., "Introducing foreign genes into fish eggs with electroporated sperm as a carrier," *Mol. Mar. Biol. Biotechnol.,* 1(4/5):276–281 (1992).

Müller et al., "Efficient transient expression system based on square pulse electroporation and in vivo luciferase assay of fertilized fish eggs," *FEBS Lett.,* 324(1):27–32 (1993).

Murakami et al., "Micromachined electroporation system for transgenic fish," *J. Biotechnol.,* 34:35–42 (1994).

Ozato et al., "Production of transgenic fish: introduction and expression of chicken δ-crystallin gene in medaka embryos," *Cell Differ.,* 19:237–244 (1986).

Postlethwait et al., "Zebrafish genomics: from mutants to genes," *Trends Genet.,* 13(5):183–190 (1997).

Powers, "Fish as Model Systems," *Science,* 246:352–358 (1989).

Powers et al., "Electroporation: a method for transferring genes into the gametes of zebrafish (*Brachydanio rerio*), channel catfish (*Ictalurus punctatus*), and common carp (*Cyprinus carpio*)," *Mol. Mar. Biol. Biotechnol.,* 1(4/5):301–308 (1992).

Riley et al., "Efficient induction of point mutations allowing recovery of specific locus mutations in zebrafish," *Proc. Natl. Acad. Sci. USA,* 92(13):5997–6001 (1995).

Rogers et al., "Intralaboratory optimization and standardization of mutant screening conditions used for a lambda/lacI transgenic mouse mutagenesis assay (I)," *Mutation Res.,* 32:57–66 (1995).

Russell et al., "The Mouse Specific–Locus Test with Agents Other Than Radiations: Interpretation of Data and Recommendations for Future Work," *Mutation Res.,* 86:329–354 (1981).

Rüther et al., "Easy identification of cDNA clones," *EMBO J.,* 2(10):1791–1794 (1983).

Shimada et al., "Some Characteristics of Radiation–or ENU-Induced Mutations at the b Locus of the Medaka, *Oryzias latipes*," Abstract GE 3 *Zoological Sci.* (Tokyo), 7(6):1053 (1990).

Shimada et al., "Further Characterization of Radiation–or ENU–Induced Mutations at the b Locus of the Medaka, *Oryzias latipes*," Abstract, *Zoological Sci.* (Tokyo), 8(6):1127 (1991).

Singer, "All oxygens in nucleic acids react with carcinogenic ethylating agents," *Nature,* 264:333–339 (1976).

Singer et al., "Oxygens in DNA are main targets for ethylnitrosourea in normal and xeroderma pigmentosum fibroblasts and fetal rat brain cells," *Nature,* 276:85–88 (1978).

Solnica–Krezel et al., "Efficient Recovery of ENU–Induced Mutations From the Zebrafish Germline," *Genetics,* 136:1401–1420 (1994).

Streisinger et al., "Production of clones of homozygous diploid zebra fish (*Brachydanio rerio*)," *Nature,* 291:293–296 (1981).

Stuart et al., "Replication, integration and stable germ–like transmission of foreign sequences injected into early zebrafish embryos," *Development,* 103(2):403–412 (1988).

Symonds et al., "Development of a mass gene transfer method in chinook salmon: optimization of gene transfer by electroporated sperm," *Mol. Mar. Biol. Biotechnol.,* 3(2):104–111 (1994).

Szelei et al., "Entrapment of high–molecular–mass DNA molecules in liposomes for the genetic transformation of animal cells," *Biochem. J.,* 259:549–553 (1989).

Tamiya et al., "Spatial imaging of luciferase gene expression in transgenic fish," *Nucleic Acids Res.,* 18(4):1072 (1990).

Tao et al., "Comparison of somatic mutation in a transgenic versus host locus," *Proc. Natl. Acad. Sci., USA* 90(22):10681–10685 (1993).

Tennant et al., "Prediction of Chemical Carcinogenicity in Rodents from in Vitro Genetic Toxicity Assays," *Science,* 236:933–941 (1987).

Tsai et al., "Initiation of the transgenic lacZ gene expression in medaka (*Oryzias latipes*) embryos," *Mol. Mar. Biol. Biotechnol.,* 4(1):1–9 (1995).

Valcovic et al., "An Approach to Measuring Germinal Mutations in the Mouse," *Environ. Health Perspect.,* 6:201–205 (1973).

Van Beneden et al., "Oncogenes in Hematopoietic and Hepatic Fish Neoplasms," *Cancer Res.* (Suppl.), 50:5671s–5674s (1990).

Vijg et al., "Ch 29:Bacteriophage Lambda and Plasmid lacZ Transgenic Mice for Studying Mutations in Vivo," *Technologies for Detection of DNA Damage and Mutations,* Plenum Press, NY, Title page, publication page, table of contents and pp. 391–410 (1996).

Vogelstein et al., "Genetic Alterations During Colorectal–Tumor Development," *N. Engl. J. Med.,* 319(9):525–532 (1988).

Walker et al., "A Small Fish Model for Assessing Cancer Risk at Low Carcinogen Concentrations," Abstract 302, Abstracts for the 31$^{st}$ Annual Meeting of the Society of Toxicology, Feb., 1992, *The Toxicology,* 12(1):97 (1992).

Winn et al., "Transfer, Methylation and Spontaneous Mutation Frequency of ΦX174am3cs70 sequences in Medaka (*Oryzias latipes*) and Mummichog (*Fundulus heteroclitus*): Implications for Gene Transfer and Environmental Mutagenesis in Aquatic Species," *Marine Environ. Res.,* 40(3):247–265 (1995).

Yamamoto, *Series of Stock Culture in Biological Field: Medaka (killifish): Biology and Strains* 1$^{st}$ Ed., Keigaku Publishing Co., Tokyo, Title page, publication page and table of contents only, 3 pages. (1975).

Zelenin et al., "The delivery of foreign genes into fertilized fish eggs using high–velocity microprojectiles," *FEBS Lett.,* 287(1–2):118–120 (1991).

\* cited by examiner

FIG. 1

PLASMID-BASED MUTATION DETECTION SYSTEM IN TRANSGENIC FISH

This application claims the benefit of U.S. Provisional Application Ser. No. 60/105,751, filed Oct. 26, 1998.

FIELD OF THE INVENTION

This invention relates to a transgenic fish carrying a plasmid-based marker, and in particular relates to a transgenic fish for use in evaluating the effect of a potential mutagen. The transgenic fish is exposed to the mutagen, and mutagenesis is detected by assaying for a mutation target nucleic acid sequence present as a genomically integrated transgene in the transgenic fish.

BACKGROUND OF THE INVENTION

The health risk posed by exposure to mutagenic agents in the environment remains an important concern as it is known that induction of mutations may lead to various somatic or inherited diseases. In particular, cancer has been shown to result from a series of mutations in specific oncogenes and tumor suppressor genes (Vogelstein et al., *N. Engl. J. Med.* 319: 525–532 (1988)). Despite the recognition of the role of induced mutation as an important event leading to disease, there are few methods available for the assessment of genetic hazard, or focus on the study of gene mutations as they occur at the DNA level in vivo. As a result, there is an immediate need to develop sensitive and biologically relevant methods that can be applied to the study of the mechanisms of mutagenesis and hazard assessment.

There are two practical requirements common to any study of mutagenesis: 1) the specific loci to be examined should be sensitive to mutation induction, and 2) the mutants must be recovered in sufficient numbers. Until recently, progress in the analysis of gene mutations directly at the DNA level was limited by the standard molecular techniques and the available endogenous genes. During past volts, the most relevant assays for induction of transmissible mutations have been based on the appearance of visible or biochemical mutations among the offspring of exposed mice (L. B. Russell et al., *Mutation Res.* 86: 329–354 (1981); L. R. Valcovic et al., *Environ. Health Perspect.* 6:201–205 (1973); S. E. Lewis et al., *Prog. Clin. Biol. Res.* 209B. 359–365 1986)). These tests cannot be practically applied to large numbers of compounds because they require extensive resources and very large numbers of animals. The tests also fail to provide information regarding somatic mutagenesis or clustering of mutations, which may be important in the understanding of the development of various diseases.

In order to circumvent some of the problems inherent in rodent assays, short-term mutagenicity tests were developed, based on the assumption that many of the chemicals toxic to rodents would also be genotoxic to bacteria. However, an analysis by the National Toxicology Program (R. W. Tennant et al., *Science* 236:933–941 (1987)) revealed significant differences in results between rodent and bacterial tests. This failure of predictive correlation may be related to: 1) a lack of understanding of the roles mutation plays in cell transformation, and 2) differences between animals and bacterial cells in terms of exposure, biological milieu, metabolism, replication and repair. While comparisons between animals and animal cells in culture provide appropriate genomic similarity, there are few known biological markers for mutation of cells in culture. The biological markers that have been identified are restricted to specific cell types and therefore are of limited use for in vivo comparisons.

There thus remains a need to combine the simplicity of short-term in vitro assays with in vivo studies. Ultimately, reliable and realistic hazard assessment and informative mechanistic studies of mutagenesis require the development of practical methods for evaluating somatic and genetic events in whole animals exposed to environmental agents. New approaches that use recombinant DNA and gene transfer techniques to develop transgenic animal models offer significant promise for in vivo studies of mutagenesis, cancer, birth defects and other diseases (T. L. Goldsworthy et al., *Fund. Appl. Toxicol.* 22:8–19 (1994)). Transgenic rodents that carry genes specifically designed for the quantitation of spontaneous and induced mutations are currently available and represent a major advance in the study of mutagenesis by allowing rapid analysis of tissue-specific mutations in a whole organism following mutagenic agent exposure (J. C. Mirsalis et al.,*Ann. Rev. Pharmacol. Toxicol.* 35:145–164 1995)).

To be effective, the transgenic approach as applied to mutagenesis should include the following components: 1) unique genes with known sequences; 2) a capacity to observe changes at the single gene copy level; 3) an easily attainable sample population of sufficient size to allow measurement of low frequency events; and 4) the ability to determine the exact nature of the mutation, independent of the host phenotype. Transgenic mutagenesis assay systems based on this approach rely on bacteriophage or plasmid shuttle vectors to carry a mutation target. The basic principle in this approach is that a recombinant gene which carries a mutation target (shuttle vector) is introduced into a host genome. Following exposure to a mutagen, the target gene is recovered to serve as an indicator of mutagenesis (reviewed by R B. Dubridge et al., *Mutagenesis* 3(1):1–9 (1988)).

Shuttle vectors currently in use include both bacteriophage-based and plasmid-based vectors. For example, the lambda ($\lambda$) bacteriophage-based recombinant vector combines cos site packaging for recovery of the phage sequence from the host DNA and uses the lacI, lacZ or cII genes as the target gene (J. S. Lebkowski et al., *Proc. Natl. Acad. Sci.* 82:8606–8610 (1985); J. A. Gossen et al., *Proc. Natl. Acad. Sci.* 86:7971–7975 (1989); J. L. Jakubczak et al., *Proc. Natl. Acad. Sci. U.S.A.*, 93:9073–9078 (1996)). Another system is based on the pUR288 plasmid vector which contains the lacZ sequence as the mutation target (M. Boerrigter et al., *Nature* 377:657–659 (1995); M. Dollé et al., *Mutagenesis* 11:111–118 (1996)). In both the $\lambda$ and plasmid-based assays, mutation-induced inactivation of the lac genes are then detected histologically in *E. coli*. Another system is based on the bacteriophage $\phi$X174 integrated shuttle vector in which the vector is recovered by transfection. This vector is recovered from the transgenic host, transfected into a suitable *E. coli* host, and mutations at specific locations in the phage sequence are identified by suppressor-mediated selection on permissive and nonpermissive *E. coli* (H. V. Malling et al., *Mutation Res.* 212:11–21 (1989); R. N. Winn et al., *Marine Environ. Res.* 40(3):247–265 (1995)).

A fundamental limitation of the bacteriophage-based mutation detection systems is their apparent inability to detect large-scale DNA deletions characteristically induced by clastogenic agents such as ionizing radiation (K. Tao et al., *Proc. Nat'l. Acad. Sci, U.S.A.*, 90:10681–10685 (1993)). Most deletions reported thus far in the abased systems have only been 1–23 base pairs in length. Deletions in the range of hundreds of base pairs are rarely reported using bacteriophage-based mutagenesis detection assays (G. Douglas et al., *Mutagenesis* 9:451–458 (1994)). Current estimates, depending upon the particular test system, are that up to 90% of radiation-induced mutations are thought to be DNA deletions. The bacteriophage shuttle-vector systems seem to have an inherent bias against detecting certain types of deletions primarily due to restrictive packaging and recovery requirements. It is speculated that since two intact cos-sites are required for the packaging of a single λ vector, any deletions that extend into regions adjacent to a transgene concatamer may prevent vector recovery.

A plasmid-based process for detecting mutations in whole animals is described in Gossen et al. (U.S. Pat. No. 5,602, 300), but is limited to use in transgenic mammals, namely rodents. The plasmid pUR288, which contains a pBR322 Ori for replication, the ampicillin gene, and the whole lacZ gene including the lacZ operator sequence, was inserted into a bacteriophage lambda vector and transferred to the germ line of a mouse by means of microinjection of fertilized egg cells. The lacz-containing plasmid was purified from chromosomal DNA of a resulting transgenic mouse by treating the genomic DNA with a restriction enzyme (also known as a restriction endonuclease), then contacting the restriction digest to a solid support comprising LacI repressor protein (i.e., a lacZ operator binding material) to bind and isolate the plasmid. Gossen et al. (*Mut. Res.* 331:89–97 (1995)) also disclose incorporation of the linearized form of the plasmid directly into mammalian DNA (without using a bacteriophage vector); and detection of mutations in the lacZ gene by plasmid rescue as well as bacteriophage rescue. Vijg et al. (U.S. Pat. No. 5,817,290) teach a similar plasmid-based method for detection of mutations, except that the plasmid vector is recovered by simultaneously excising it from genomic DNA and contacting it with the solid affinity suppport.

There remains a need for an improved mutagenesis assay detection system capable of detecting mutagenic events that may be missed by bacteriophage-based systems. Additionally, alternative animal models are needed to extend and improve methods used to assess the potential genetic health risks posed by exposure to mutagens the environment.

SUMMARY OF THE INVENTION

A transgenic fish has been developed for use in a plasmid-based mutagenesis detection system. The system allows in vivo quantitation of By spontaneous and induced mutations using a recoverable mutation target nucleic acid sequence and assay system. After exposure of the transgenic fish to a mutagen, DNA is extracted from the fish tissue, and the mutation target nucleic acid sequence is recovered and analyzed for mutagenesis, preferably using a bioassay in indicator bacteria. In a preferred embodiment, the mutagenesis detection system of the invention is based on the pUR288 plasmid.

The transgenic fish of the invention is one whose somatic and germ cells contain at least one genomically integrated copy of a plasmid carrying an assayable mutation target nucleic acid sequence. The plasmid is preferably one that is suitable for cloning into *E. coli*. The invention further provides a transgenic fish gamete, including an transgenic fish egg or sperm cell, a transgenic fish embryo, and any other type of transgenic fish cell or cluster of cells, whether haploid, diploid, triploid or other zygosity having at least one genomically integrated copy of a plasmid comprising a mutation target nucleic acid sequence. As used herein, the term "embryo" includes a single cell fertilized egg (i.e., a zygote) as well as a multicellular developmental stage of the organism. Preferably, the plasmid is integrated into the fish's somatic and germ cells such that it is stable and inheritable. The transgenic fish or fish cell preferably contains a multiplicity of genomically integrated copies of the plasmid; more preferably, the multiple copies of the plasmid are integrated into the host organism's genome in a contiguous, head-to-tail orientation. Progeny of the transgenic fish containing at least one genomically integrated copy of the plasmid, and transgenic fish derived from a transgenic fish egg, sperm, embryo or other fish cell of the invention, are also included in the invention. A fish is "derived from" a transgenic fish egg, sperm cell, embryo or other cell if the transgenic fish egg, sperm cell, embryo or other cell contributes DNA to the fish's genomic DNA. For example, a transgenic embryo of the invention can develop into a transgenic fish of the invention; a transgenic egg of the invention can be fertilized to create a transgenic embryo of the invention that develops into a transgenic fish of the invention; a transgenic sperm cell of the invention can be used to fertilize an egg to create a transgenic embryo of the invention that develops into a transgenic fish of the invention; and a transgenic cell of the invention can be used to clone a transgenic fish of the invention. In some preferred embodiments of the invention, the transgenic fish is sterile. The present invention further includes a cell line derived from a transgenic fish embryo or other transgenic fish cell of the invention, which contains at least one copy of a plasmid carrying an assayable mutation target nucleic acid sequence.

The mutation target nucleic acid sequence is preferably one having a characteristic or function, or encoding a gene product having a characteristic or function, that is detectably altered when mutated, thereby allowing the nonmutated form of the nucleic acid sequence to be distinguished from the mutated form. In a particularly preferred embodiment, a mutation in the mutation target nucleic acid sequence is detectable via bioassay in a bacterial cell, such as an *E. coli* cell, into which a mutation target nucleic acid sequence that has been isolated from the fish or fish cell has been introduced. In this regard, a transgenic fish having a triploid genome is desirable because triploidy allows larger amount of DNA to be recovered. An increase in the amount of DNA recovered has many advantages. For example, it allows for more efficient detection of the mutation target nucleic acid. Moreover, fish having a triploid genome are typically sterile, which may be desirable for certain applications or studies. The assayable mutation target nucleic acid sequence is typically heterologous with respect to the fish genome. Preferably, the plasmid is integrated into the host organism's genome in a manner that avoids causing a detectable mutation in an endogenous gene of the host, thereby avoiding undesirably high background levels of mutation and reducing the sensitivity of the assay. The use of a smaller vector is preferred because the small size reduces the likelihood of physical disruption of one of the host cell's genes. Preferred mutation target nucleic acid sequences include the lacI gene, the lacZ gene, the lac promoter sequence, and the rpsL gene. Preferably, the lacZ gene includes the lacZ promoter.

In another embodiment, the invention includes a genomically identical population of transgenic fish, each of whose somatic and germ cells contain at least one genomically integrated copy of a plasmid comprising an assayable mutation target nucleic acid sequence. The genomically identical population is a unisex population and can be male or female. Preferred embodiments of the genomically identical transgenic fish population are essentially as described for the transgenic fish of the invention. In an alternative embodiment, the invention includes a population of transgenic fish, i.e., an in-bred line, the members of which are not necessarily genomically identical but are homozygous with respect to genomically integrated plasmid.

Also provided is a method for mutation detection utilizing the transgenic fish or fish cell of the invention. This method is useful in evaluating the mutagenicity of various potential mutagens, such as chemical compounds, radioisotope emissions, and electromagnetic radiation. Mutations are detected in a mutation target nucleic acid sequence of a plasmid, wherein at least one copy of the plasmid has been integrated into the genomic DNA of the fish or fish cell. DNA containing the mutation target nucleic acid sequence is first recovered from the transgenic fish or fish cell, preferably by extracting the fish or fish cell DNA from the fish or fish cell, then cleaving the extracted DNA with a restriction endonuclease to yield at least one DNA fragment comprising the mutation target nucleic acid sequence derived from the plasmid, and multiple DNA fragments comprising chromosomal DNA. The DNA fragment that includes the mutation target nucleic acid sequence preferably includes substantially the entire plasmid, although it can contain a portion of the plasmid DNA, as long as it contains the mutation target nucleic acid sequence. Optionally, the method of mutation detection farther comprises separating the DNA fragment comprising the mutation target nucleic acid sequence from the multiple chromosomal fragments to isolate the mutation target DNA, although it should be understood. flat separation of the cleaved fragments comprising the mutation target DNA from the remaining chromosomal DNA is not required by the present method. If separation of the fragments is performed, the cleavage and the separation steps can be performed sequentially, or they can be performed simultaneously. In a particularly preferred embodiment of the method of the invention, wherein the mutation target nucleic acid sequence contains the lacZ gene, cleaved DNA fragments are separated by contacting the fragments with an affinity support comprising a lacZ operator binding material so as to immobilize the DNA fragment containing the mutation target nucleic acid sequence. After washing away the unbound DNA fragments, the bound DNA fragment is eluted from the support. The method further includes detection of the presence of a mutation in the mutation target nucleic acid sequence. Where the mutation target nucleic acid sequence contains the lacZ gene, mutations in the gene are preferably detected by transforming a host restriction-negative, lacZ$^{--}$, galE$^-$ bacterial host with cleaved DNA comprising the mutation target nucleic acid sequence (whether or not the DNA fragments containing chromosomal DNA have been separated out); culturing the transformed bacteria on a lactose-containing or lactose analogue-containing medium; and selectively detecting a bacterial host that contains a mutation in the lacZ gene. Growth of the bacterial host is indicative of the existence of a mutation in the lacZ gene. Optionally, prior to transforming the bacterial host, the DNA comprising the mutation target nucleic acid test region is ligated to yield a circular DNA that is more efficiently electroporated. Also optionally, mutations in the mutation target nucleic acid sequence can be further analyzed, for example by nucleic acid sequence determination. When used to evaluate the mutagenicity of a particular agent, condition or event, the method further comprises, prior to extracting the fish DNA, exposing the transgenic fish or fish cell to the suspected mutagen.

The invention further includes a method for evaluating the mutagenicity of a suspected mutagen. A transgenic fish or fish cell of the invention is exposed to a suspected mutagen; the DNA containing the mutation target nucleic acid sequence is recovered from the transgenic fish or fish cell; and the presence of a mutation in the mutation target nucleic acid sequence is detected. Optionally, the mutated target nucleic acid sequence can be analyzed, for example by nucleic acid sequencing and the constructing a mutation spectrum.

Also included in the invention is a method for making a transgenic fish. Heterologous DNA is injected into a one-cell fish embryo, preferably through the micropyle, within about 10 minutes following fertilization, preferably within about 5 minutes following fertilization. A method for making a transgenic fish for mutagenesis detection includes microinjecting heterologous DNA into a one-cell fish embryo, wherein the heterologous DNA comprises a mutation target nucleic acid sequence, such as a lacZ gene.

The invention further includes a kit for detecting mutagenesis in transgenic fish comprising a genomically integrated plasmid comprising a mutation target nucleic acid. The kit includes, separately packaged, a host restriction-negative bacterial strain and a solid support that includes binding material capable of binding at least a portion of the plasmid. When used to detect mutagenesis in a transgenic fish having the lacZ gene as its mutation target nucleic acid sequence, the bacterial strain is preferably a host restriction-negative, lacZ$^-$, galE$^-$ $E.$ $coli$ strain, and the solid support preferably includes a lac operator binding material such as β-galactosidase/LacI repressor fusion protein. The kit can optionally contain one or more additional components, such as a binding buffer to promote binding of the plasmid to the solid support, one or more restriction enzymes to excise the plasmid from the genomic DNA of the transgenic fish, an excision buffer, and a ligation for circularization of the excised plasmid prior to introduction of the plasmid into the bacterial host. The ligation buffer preferably contains a ligase, such as T4 ligase. The binding buffer and the excision buffer can, but need not be, the same buffer, so as to allow simultaneous excision of the plasmid and binding of the plasmid to the solid support.

BRIEF DESCRIPTION OF THE DRAWINGS

FIG. 1 is a schematic representation of plasmid pUR288 (U.

Rüther et al., EMBO J. 2(10):1791–1794 (1983); J. Gossen et al., *Mut. Res.* 331:89–97 (1995); Gossen et al. (U.S. Pat. No. 5,602,300)).

DETAILED DESCRIPTION

The present invention provides a transgenic fish and fish cell, along with methods for detecting mutations in the DNA of a transgenic fish or a transgenic fish cell. The DNA of the transgenic fish of the invention contains one or more copies of a linearized plasmid containing a mutation target nucleic acid sequence, preferably a lacZ gene. Preferably, the lacZ gene includes the lacZ operator sequence. In a particularly preferred embodiment of the transgenic fish and method of the invention, the entire lacZ gene serves as the mutation target, and the lacZ operator sequence provides an opportunity for rapid and efficient purification of DNA. To detect mutations in the target gene, the plasmid is first rescued from the fish genomic DNA by extracting DNA from the cells of the transgenic fish or the transgenic fish cell, then the isolated DNA is fragmented, preferably by treatment with a restriction enzyme selected to excise the plasmid DNA from the chromosomal DNA. The plasmid-derived DNA is optionally isolated from the remaining genomic DNA, preferably by contacting the restriction digest with an affinity support containing a binding material that preferentially binds to a nucleic acid sequence in the plasmid-derived DNA. In embodiments wherein the mutation target nucleic acid sequence includes the lacZ gene, the affinity support preferably includes a binding material that binds the lacZ operator, for example as β-galactosidase/LacI repressor fusion protein (also known as a LacZ/LacI fusion protein. DNA that does not bind to the binding material is removed, and the plasmid-derived DNA is eluted from the support. The plasmid-derived DNA is optionally circularized, then transformed into a bacterial host wherein a bioassay can be performed to detect the existence of a mutation in the mutation target nucleic acid sequence. In a preferred embodiment wherein the mutation target nucleic acid sequence comprises a lacZ gene, the bacterial host is preferably a restriction-negative, lacZ⁻⁻, galE⁻⁻ bacterial host. In that system mutants are identified by culturing the transformed bacterium on a lactose-containing or lactose analogue-containing medium. Only bacteria which exhibit partial or no β-galactosidase activity can grow on this medium; growth is thus indicative of a mutation in the lacZ gene. If desired, the mutated target nucleic acid sequence can be sequenced to determine the type, location and extent of mutation, using, for example, a modified polymerase chain reaction (PCR) method or subdloning.

Various agents can be tested for mutagenic properties by exposing one or more transgenic fish of the invention to a suspected mutagen, then detecting mutations in the mutation target, e.g., the lacZ gene as described herein. In an analogous manner, the mutagenicity of various agents can be tested in vitro using cultured transgenic fish cells of the invention. The term "mutagen" is to be broadly understood as meaning any mutagenic or potentially mutagenic agent, event, or condition including a mutagenic chemical compound, such as a toxicant; radioactivity, including but not limited to alpha, beta, or gamma emissions from an radioisotope; electromagnetic radiation of any wavelength or frequency, such as x-ray, ultraviolet, or infrared radiation; exposure to a magnetic field or an electromagnetic field (EMF), and the like.

The transgenic fish or fish cell of the invention comprise one or more copies of the plasmid containing the mutation target nucleic acid sequence. A transgenic fish whose somatic and germ cells comprise at least one genomically integrated copy of the plasmid represents a preferred embodiment; more preferably, multiple copies of the plasmid are genomically integrated into the somatic and germ cells of the fish, most preferably in a head-to-tail orientation. The transgenic fish of the invention is preferably a teleost (boney) fish, but also includes a cartilaginous fish. Conveniently, the transgenic fish can be selected from among the well-known group of laboratory model fish which include medaka, zebrafish, mummichog, killifish, channel catfish, common carp and trout. Medaka, zebrafish or Fundulus spp. (for example, mummichog or killifish) are particularly preferred. In a highly preferred embodiment, the transgenic fish of the invention are the Japanese medaka (*O. latipes*) and the estuarine killifish (*F. heteroclitus*).

The invention also provides a genomically identical population of transgenic fish, each fish comprising one or more copies of the plasmid containing a mutation target nucleic acid sequence. A "genomically identical" population of transgenic fish is one wherein each fish has the same genomic DNA as the others in the population; this can also be referred to as a clonal population. Members of a genomically identical population are produced by cloning or inbreeding within the population rather than by mating with non-genomically identical fish (see, e.g., D. C. Streisinger et al., *Nature*, 291:293–296 (1981); W. Driever et al., *Trends Genet.*, 10 (5): 152–159 (1994)). Zygosity of the genomically identical population can be haploid, diploid or triploid. A genomically identical population is a single sex (unisex) population and can be male or female. A genomically identical female population can be produced, for example, by gynogenesis, wherein sperm is used to activate the egg but does not contribute genomic DNA to the developing organism (J H. Postlethwait et al., *Trends Genet.*, 13(5):183–190 (1997)). Methods for making a genomically identical male population include heat shock, pressure shock, or irradiation, in combination with appropriate breeding techniques.

Although introduction of the plasmid into a host fish cell is not limited to any particular mode of delivery, microinjection is preferred. Microinjection is labor-intensive and time-consuming, but when practiced in accordance with the present invention results in a greater likelihood of introducing the DNA into the cell nucleus as opposed to the cytoplasm. While advances have been made relating to other methods of gene transfer such as electroporation of eggs (e.g., K. Inoue et al., *Cell Differ. Dev.* 29(2):123–128 (1990); F. Muller et al., *FEBS Lett.*, 324 (1):27–32 (1993); Y. Murakami et al., *J. Biotechnol.*, 34 (1):35–42 (1994); F. Muller et al., *Mol. Mar. Biol. Biotechnol.* 1 (4–5):276–81 (1992)) and sperm (Symonds et al., 1994; D. A. Powers et al., *Mol. Mar. Biol. Biotechnol.*, 1 (4–5):301–8 (1992)); particle gun bombardment (A. V. Zelenin et al., *FEBS Lett.*, 287 (1–2):118–20 (1991); liposomes (J. Szelei et al., *Biochem. J.*, 259 (2):549–53 (1989); and retroviral vectors (J. K. Lu et al., *Mol. Mar. Biol. Biotechnol.*, 6 (4):289–95 (1997)); these procedures only rarely result in transgen integration and germline transmission in fish (K. Inoue et al., *Cell Differ. Dev.* 29(2):123–128 (1990). Nonetheless, the invention is not intended to be limited to any particular method of introducing the heterologous DNA into the host organism. Preferably, the plasmid sequences are stably integrated into the host genome and are inheritable.

Figure 1:
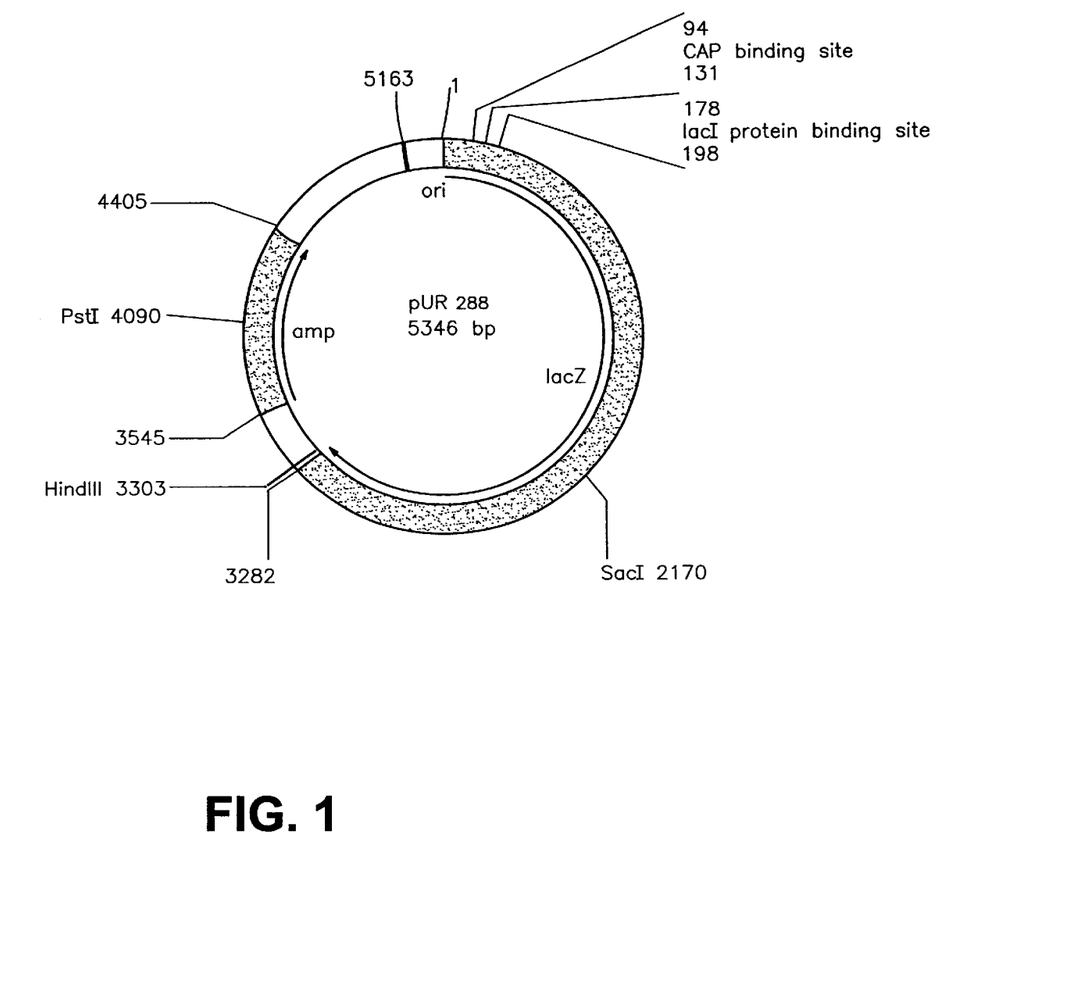

The plasmid used to transform the fish contains an assayable mutation target nucleic acid sequence. An "assayable" mutation target nucleic acid sequence is one wherein a mutated form of the nucleic acid sequence can be distinguished from the nonmutated form of the nucleic acid sequence, either directly or indirectly, as by using a laboratory assay or other detection procedure. For example, mutation of the mutation target nucleic acid sequence can result in a detectable change in the function of the nucleic acid sequence, or of a gene product encoded thereby. Preferably, the presence or absence of a mutation in the nucleic acid sequence is detectable by way of a chemical or biological assay. Preferably, the mutation target nucleic acid sequence includes a lad gene, a lacZ gene, a lac promoter sequence or an rpsL gene from *E. coli*. More preferably, it includes a lacZ gene, most preferably a lacZ gene that includes a lacZ operator. Inclusion of the lacZ operator allows rapid and efficient purification of the plasmid, as described above. Optionally the plasmid further includes an origin of replication (an ori), preferably a pBR322 ori, a selection marker gene, or both. A selection marker gene typically encodes a polypeptide which can confer a phenotypic characteristic to the transformed cell, such as antibiotic resistence, test compound metabolism, and the like. An ampicillin-resistance gene is an example of a suitable a selection marker gene. A representative preferred embodiment of the plasmid used to transform the fish according to the invention is pUR288

(FIG. 1). The plasmid pUR288 contains certain features common to preferred plasmids of the invention, namely the entire lacZ gene sequence (as the mutation target gene) including the lacO sequence (to allow affinity capture with the LacI repressor protein), together with the ColE1 and a marker gene, in this case the amp$^R$ gene, to allow propagation and selection in *E. coli* (U. Rüther et al., EMBO J. 2(10):1791–1794 (1983)). The plasmid contains restriction sites, such as HindIII restriction sites in the case of pUR288, positioned to allow excision of the genomically integrated plasmid from the fish DNA. These restriction sites are located at or near each of the two ends of the linearized plasmid and thus flank the lacZ gene. The plasmid is incorporated directly into the fish DNA in a linearized form. Preferably, the plasmid vector used for transformation of the fish host cell comprises multiple end-to-end copies of the plasmid in a concatemeric configuration. The restriction sites are positioned between each copy of the plasmid, such that digestion with the appropriate restriction endonuclease releases monomeric plasmid sequences (single copies of the plasmid). It is not necessary, nor is it desirable, to insert the plasmid into a bacteriophage vector prior to insertion into the host's chromosomal DNA.

In a preferred embodiment, the plasmid is one that is suitable for transformation of bacteria, preferably *E. coli*. A host restriction-negative bacterial cell is preferred for use in the bioassay to detect the presence of mutations in the mutation target nucleic acid sequence. In a host-restriction negative bacterial cell, degradation of methylated plasmid DNA is prevented (the plasmid DNA is likely to have been methylated while in the fish host). When the mutation target nucleic acid sequence includes the lacZ gene, the preferred host cell is a host restriction-negative, lacZ$^{--}$, galE$^{--}$ *E. coli* strain. Non-mutant colonies do not survive in this preferred selection system; only those cells which have incorporated a mutated plasmid will grow after plating on the lactose-containing or lactose analogue-containing medium. *E. coli* cells that have incorporated a non-mutated plasmid will convert lactose or its analogue to galactose as a result of the presence of β-galactosidase. Further conversion of galactose is however not possible in the bacterial host due to the mutation in the galE gene. This leads to an accumulation of the toxic by-product UDP-galactose, whereby the host cell dies. Mutant colonies that produce no β-galactosidase survive because they do not convert the lactose or the lactose analogue to galactose. Mutants that exhibit residual levels of β-galactosidase activity also may grow to some degree on media containing lactose or a lactose analogue (M. Boerrigter, *Env. Mol. Mutagenesis* 32, 148–154 (1998) and are thereby distinguishable from nonmutants, which do not grow at all. It should be understood that the invention is not limited to the use of *E. coli* as the bacterial host; other types of bactena can also be used as long as suitable vector plasmids and host-restriction negative strains are available.

The plasmid is, of course, heterologous with respect to the host fish, the terms "heterologous" and "exogenous" being used herein interchangeably to denote nucleic acid sequences that have been inserted in to a host organism, but are not found in the normal genetic complement (i.e., genome) of the host organism. A gene that is heterologous with respect to an organism into which it has been inserted or transferred is sometimes referred to herein as a "transgene." A "transgenic" animal or host is an animal having one or more cells that contain exogenous (heterologous) nucleic acid sequences, including expression vectors.

Mutations in the mutation target nucleic acid harbored by the transgenic fish or fish cell of the invention are detected by first extracting DNA from the cells of the fish or fish cells, then the fragmenting the isolated DNA by treatment with a restriction endonuclease selected to excise the plasmid DNA from the chromosomal DNA. Techniques for genomic DNA extraction are well-known and any convenient method can be employed; however methods particularly suited for fish are performed using gentle tissue homogenation and proteolytic digestion at about 37° C. as described further in Example I. The restriction endonuclease recognizes restriction sites flanking the lacZ operon which have been engineered into the plasmid, so as to cut out or excise the DNA of the plasmid. It should be understood that the plasmid is considered to be excised if the restriction enzyme liberates the entire mutation target region (e.g., the lacZ gene); in other words, the restriction sites are at or near the two ends of the linearized plasmid and the plasmid thus released may be somewhat truncated in comparison to the plasmid originally transformed into the fish or fish cell. This could occur, for example, where the restriction endonuclease used to liberate the plasmid is different from the restriction endonuclease used to linearize the plasmid prior to introduction into the fish or fish cell. Preferably, the restriction endonuclease does not recognize a restriction site internal to the mutation target nucleic acid sequence. When pUR288 is used as the plasmid, a convenient restriction enzyme is Hind III.

If desired, the fragmented DNA present in the resulting restriction digest can be subjected to a separation protocol that separates the fragments containing the plasmid-derived mutation target nucleic acid sequence from the remaining fragments containing chromosomal DNA. Isolation of plasmid-derived DNA fragments can be effected using any convenient means such as affinity chromatography, gel electrophoresis, size exclusion chromatography, centrifugation or spin filtration, dialysis, and the like. Because of the efficiency of genomic integration, separation of the DNA fragments is optional, and the bacterial host can be transformed with either isolated or nonisolated plasmid-derived DNA fragments. When the mutation target nucleic acid sequence comprises the lacZ gene including the lacZ operator, the fragmented DNA is preferably and conveniently subjected to affinity purification using a lacZ-operator binding material. The lacZ operator binding material binds the lacZ operator present in the plasmid DNA. Affinity binding of the plasmid is preferably carried out on a solid support, more preferably on solid particles, most preferably on magnetic beads. The support is coated with a lacZ operator binding material. The lacZ operator binding material preferably comprises a protein. A lacZ operator binding protein can be an antibody with affinity for the lacZ operator, LadI repressor protein, or a LacI repressor fusion protein such as lacI repressor/β-galactosidase fusion protein or a LacI repressor/Protein A fusion protein. This material can be bound directly to the solid support but is preferably bound indirectly to the solid particles. Beads and reagents are commercially available from Dynel (Oslo, Norway). Anti-βgalactosidase and LacI repressor/β-galactosidase fusion protein are typically successively bound to the solid particles. After contact of the organism's genomic DNA with the solid support and removal of the unbound DNA fragments, the bound DNA fragment is eluted from the support using one or more agents having greater affinity for the LacI repressor or the lacZ operator than the LacI repressor and the lacZ operator have for one another. Preferably, plasmid DNA is released from the solid support using isopropyl β-D-thiogalactoside (IPTG), which eliminates the binding between the LacI repressor and the lacZ operator. Affinity purification typically removes essentially all the excess chromosomal DNA, and circularization of the plasmid can be efficiently performed thereafter in a small volume.

Prior to transformation into the bacterial host, the plasmid-derived DNA is preferably circularized by ligation, for example enzymatic ligation using T4 ligase. The plasmid-derived DNA is then transformed into the bacterial host using methods well-known in the art. Typically, the circularized plasmid is electroporated into the bacterial host. Mutants are identified by selective growth on the culture medium, as described herein.

Mutation Analysis

The transgenic fish of the invention can be used for mutagenesis testing by exposing it to potential mutagenic agent. A mutated target sequence can be subjected to nucleic acid sequencing to determine the mutation spectrum characteristic of a particular mutagen, or of a particular tissue, or of the action of a particular mutagen on a particular tissue. Mutation spectra reflect the frequency of certain specific types of mutations in a population of mutants. Types of mutations include, for example, nucleotide transitions (G/C to A/T and A/T to G/C), nucleotide transversions (G/C to T/A, G/C to C/G, A/T to T/A, and A/T to C/G), and frameshift mutations (e.g., +1, +2, −1 and −2). Alternatively, mutations can be identified using single nucleotide polymorphism analysis, or any other method known in the art for identifying or detecting single site mutations, insertions, deletions and frameshifts.

The mutation spectrum of a population of mutants can provide much useful information. The spectrum may be characteristic of a particular mutagen or class of mutagens, and can help identify the nature of the mutagenic compound. In some instances, a change in the mutation spectrum, relative to the mutation spectrum of a control group, may be evident even though the differences in mutation frequencies (experimental vs. control) are not statistically significant. Mutation spectra analysis may also provide insight into the possible mechanism(s) of action of a particular mutagen, in different organs and tissues. In addition, mutation spectra analysis can yield information about the sensitivity of different organs or tissues to a particular mutagen.

Advantages of a Plasmid-based Mutation Detection System

A plasmid-based mutation detection system has a distinct advantage over other transgenic mutation detection systems in that it is able to detect a wide spectrum of mutations, particularly large sequence deletions or rearrangements induced by clastogenic agents such as radiation. Plasmid recovery is not as size-dependent as it appears to be the bacteriophage-$\lambda$ sequences, due to $\lambda$'s special requirements for in vitro packaging. Thus, large sequence deletions extending into the flanking regions of the host chromosomal DNA are detectable in the plasmid-based system. As a result, all types of DNA rearrangements, including the large-scale structural DNA alterations induced by such agents as ionizing radiation, can be detected with the lacZ mutation target in this system, not just point mutations (J. Gossen et al., Mut. Res. 331:89–97 (1995)). There are currently no other transgenic in vivo mutation detection systems that have demonstrated comparable capabilities.

The small size of a plasmid vector compared to a bacteriophage vector also provides several important advantages over bacteriophage-based mutation detection systems. Its smaller size facilitates genomic integration of multiple copies of the plasmid. For example, pUR288 is about 5.5 kb, approximately 1/10 the size of the bacteriophage $\lambda$ (~50 kb). The transgenic fish of the invention thus preferably carries multiple copies of the plasmid sequence which can be transmitted to its offspring. The small size of the plasmid also greatly simplifies requirements of DNA extraction, making recovery of the mutation marker more efficient. Incorporation of the lacO sequence in the plasmid vector in accordance with the present invention allows plasmid DNA to be purified from restriction-enzyme digested genomic DNA of the fish in a single step using high capacity LacI repressor magnetic beads, further increasing yields of the mutation marker. For example, pUR288 recovery is over 25 times more efficient than $\lambda$ sequence recovery (J. Gossen et al., Mut. Res. 331:89–97 (1995)). In addition to detecting a wider range of mutations, the plasmid-based system of the present invention is thus also more cost-effective than bacteriophage-based systems, and mutations can be accurately determined based on large numbers of colony forming units using small amounts of tissue. In addition, mutations are detected by a selective rather than a color procedure which reduces ambiguity in analyses.

Host Organism

There are many advantages to the use of fish to detect mutagenic agents or events. Fish are environmentally relevant models for health risk assessment of aquatic and marine systems. There is also increasing appreciation of their suitability for biomedical applications. The fish is an alternative, nonmammalian animal model that can be used to refine, reduce or replace traditional animal models used in research and testing. Fish are easily handled, manipulated, and observed without compromising natural development, and present opportunities for studies on multiple exposure routes via aqueous media. They exhibit excellent agent-specific responses to a variety of toxicants. Teleost fish, also known as the modem boney fishes, constitute the largest and most diverse division of vertebrates, with over 20,000 known species. Their diversity and phylogenetic positions make them ideal for comparative toxicological studies, which may allow more insight into basic mechanisms than would studies limited to mammalian models alone (D. A. Powers, Science 246:352–358 (1989)). Certain teleost fish, commonly referred to as laboratory aquarium fish or laboratory model species, have been extensively studied in research settings and are thus especially well-suited as transgenic hosts. Laboratory model species include, but are not limited to, medaka (Oryzias latipes), zebrafish (Danio rerio), mummichog (Fundulus heteroclitus), killifish (Fundulus spp.), channel catfish (Ictalurus punctatus), common carp (Cyprinus carpio) and trout (Salmo gardneri). Cartilagenous fish such as sharks and rays, also known as chondrichthyes fish, are also suitable transgenic host organisms.

In addition to playing an important role in comparative mutagenesis studies, it is anticipated that the transgenic fish models may ultimately facilitate a broad range of exposure regimens such as long-term low-dose chronic exposures, controlled field-based in situ exposures or large-scale mesocosms, that were previously difficult or impossible to perform. Fish can be conveniently used for zygote-to-adult exposure studies, and offer flexibility in study designs related to numbers of exposure groups and exposure schedules.

Fish eggs are relatively large, abundant, and often translucent, and can be fertilized in vitro. The resulting embryos are easily maintained and develop externally, obviating the need for reintroduction of the embryo into a receptive female. In addition, laboratory analyses can generally be performed more rapidly and at lower cost compared to rodent assays.

Heterologous genes have been introduced into fish beginning in 1984. Among these heterologous genes that have been introduced into fish include genes that code for growth hormones (human, rat, rainbow trout), chicken delta-crystalline protein, *E. coli* β-galactosidase, *E. coli* neomycin-resistance, and anti-freeze protein. However, numerous problems have been encountered in producing transgenic fish having stable, inheritable genomically integrated transgenes. For example mosaicism, which results from the failure of the transgene to integrate into the host's genomic DNA at the first mitotic division, is a common problem in the creation of transgenic fish. Mosaic organisms do not contain the transgene in every somatic and germ cell, and thus may not be capable of producing transgenic offspring. Mosaicism is presumed to arise from fact that microinjection of heterologous DNA into a fish embryo often delivers the heterologous DNA to the cytoplasm rather than the cell nucleus.

Despite the evolutionary distance between fish and humans, there is increasing evidence for correlation between environmentally-induced fish and human diseases. Fish can be exposed to different concentrations of known or suspected toxicants and can provide fundamental information related to substance toxicity and carcinogenicity/mutagenicity. The use of fish in carcinogenesis research, in particular, has received considerable attention related to the potential of fish for identifying and predicting human health effects (W. F. Hawkins et al., Chapter 14 in G. M. Rand, ed., Fundamentals of Aquatic Toxicology: Effects, Environmental Fate, and Risk Assessment, Taylor and Francis. 421–446 (1995); J. D. Hendricks, In L. J. Weber, ed., Aquatic Toxicology, Raven Press, New York. 149–211 (1982); J. J. Black, In J. Saxena, ed., Hazard Assessment of Chemicals: Current Developments, Vol. 3. Academic Press, New York. 181–232 (1984); C. D. Metcalfe, *CRC Rev. Aquat. Sci.* 1:111–129 (1989)). The fact that many fish species appear to be sensitive to the carcinogenic effects of certain chemicals while having low spontaneous rates of neoplasia supports the use of fish in various assays as alternatives or supplements to rodent chronic bioassays (G. D. Bailey et al., *Envirion. Health Perspect.* 71:147–153 (1987); T. Ishikawa et al., *J. Toxicol. Environ. Health* 5:537–550 (1979); P. Masahito et al., *Jpn. J. Cancer Res.* 79:545–555 (1988)).

The genetics, developmental biology and embryology of medaka (*Oryzias latipes*) are well-documented, and specific developmental stages have been extensively characterized (T.O. Yamamoto, Medaka (killifish): Biology and Strains. Keigaku Publishing Co., Tokyo, Japan. (1975)). Medaka is typically used to study aspects of various diseases in which large numbers of experimental organisms are required, such as in low-dose risk assessment, as well as to examine factors that only slightly increase hazard exposure risk (W. W. Walker, W. E. Hawkins, R. M. Overstreet, and M. A. Friedman, "A small fish model for assessing cancer risk at low carcinogen concentrations," *Toxicologist* 302 (1992)). The use of medaka in biomedical research, especially as a carcinogenesis model related to the potential for identifying and predicting human effects from toxicant exposure, has received considerable attention in recent years (W. E. Hawkins et al., Chapter 14 in G. M. Rand, ed., Fundamentals of Aquatic Toxicology: Effects, Environmental Fate, and Risk Assessment, Taylor and Francis. 421–446 (1995); J. D. Hendricks, In L. J. Weber, ed., Aquatic Toxicology, Raven Press, New York. 149–211 (1982); J. J. Black, In J. Saxena, ed., Hazard Assessment of Chemicals: Current Developments, Vol. 3. Academic Press, New York. 181–232 (1984); and C D. Metcalfe, *CRC Rev. Aquat. Sci.* 1:111–129 (1989)). The sensitivity of medaka to many carcinogens, the availability of specimens, and the degree of control that can be maintained over extraneous factors all contribute to this small fish being one of the most widely used species for studies in comparative toxicology (W. E. Hawkins et al., Chapter 14 in G. M. Rand, ed., Fundamentals of Aquatic Toxicology: Effects, Environmental Fate, and Risk Assessment, Taylor and Francis. 421–446 (1995)), the biology of hepatic neoplasia (D. E. Hinton et al., *Aquat. Toxicol.* 11:77–112 (1988)), oncogene activation (R. J. Van Beneden et al., *Cancer Res.* 50:5671s–5674s (1990)), DNA repair (T. Ishikawa et al., *Natl. Cancer Inst. Monograph* 65:35–43 (1984)), and mutagenesis (R. N. Winn et al., *Marine Environ. Res.* 40(3):247–265 (1995)).

Medaka offer numerous advantages for transgenic development such as small size (about 2.5 cm), relatively short generation time (1–2 months), and prolific capacity to reproduce (more than 3,000 eggs/female in a single breeding season). Spawning can be induced year-round by maintaining breeding stocks at 25–28° C. and eggs usually hatch in 10 days at 25° C. Eggs are translucent, which greatly facilitates the positioning of fine glass needles for DNA microinjection. Medaka was the first transgenic fish species produced to demonstrate successful foreign gene expression (K. Ozato et al., *Cell Differ.* 19:237–244 (1986)). Subsequently, numerous transgenic medaka have been produced that carry a variety of transgenes (e.g. K. Inoue et al., *Cell Difer. Dev.* 27(1):57–68 (1989); E. Tamiya et al., *Nucleic Acids Res.* 18:1072 (1990); K. Inoue et al., *Cell Differ. Dev.* 29(2):123–128 (1990); J. Lu et al., *Mol. Marine Biol. and Biotechnol.* 1(4/5):366–375 (1992); H. J. Tsai et al., *Mol. Mar. Biol. Biotechnol.* 4(1):1–9 (1995); R. N. Winn et al., *Marine Env. Res.* 40(3):247–265 (1995)). However, transgenic Fundulus have been produced only once (R N. Winn et al., *Marine Environ. Res.* 40(3):247–265 (1995)).

As noted above, the invention is intended to further encompass progeny of a transgenic fish containing a genomically integrated plasmid comprising a mutation target nucleic acid sequence, as well as transgenic fish derived from a transgenic fish egg, sperm cell, embryo, or other cell containing a genomically integrated plasmid comprising a mutation target nucleic acid sequence. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The hybrid progeny of these matings have the benefits of the transgene for mutation detection combined with the benefits derived from these other lineages.

EXAMPLES

The following examples, while exemplary of the present invention, are not to be construed as specifically limiting the invention. Accordingly, variations and equivalents, now known or later developed, that would be within the purview of one skilled in the art are to considered to fall within the scope of this invention.

Example I

Creation of a Transgenic Fish

Preparation of plasmid DNA

The pUR288 plasmid DNA was provided by Michaël E.T.I. Boerrigter (Leven, Inc., Bogart Georgia). In order to enhance integration of multiple copies of the plasmid pUR288, the DNA was cut with a restriction enzyme (Hind III; New England BioLabs), and then ligated into a ladder of multiple copies (4 minute ligation at 4° C. with T4 ligase (New England BioLabs), 0.5 mm ATP, 0.06 units/μl ligase, 1×ligase buffer). DNA was brought to 750 μl volume with TE (TE: 10 mM Tris, 1 mM ethylenediaminetetraacetic acid (EDTA)) and extracted twice with phenol/chloroform, once with chloroform, and precipitated with 100% ethanol. Following centrifugation, the pellet was washed with 70% ethanol, dried, and dissolved in TE at 100–200 ng/μl. Prior to microinjection, the DNA was diluted to 50–100 ng/μl in 5T.1E solution (5 mM Tris; 0.1 mM EDTA) and dialyzed on a filter over 5T.1E for 40 minutes (0.025 micron pore size, Millipore Corporation).

Microinjection of Fish Embryos

Fish embryos were microinjected generally in accordance with Winn et al. (*Marine Environ. Res.*, 40(3):247–265 (1995)), but with the modifications described herein. For medaka, in order to maximize incorporation of the gene and reduce the degree of mosaicism in the founders, fertilized eggs at the one-cell stage were collected by removing egg masses from the vent of the female fish beginning 2 hours prior to the onset of a 16 hour light-ycle and every 10–15 minutes thereafter. The gene transfer method was optimized by rigidly controlling the timing of the injection at the earliest 1-cell stage of development of the fish, in most cases within 5 minutes of fertilization. The embryos were individually separated by removing the entangling chorionic fibrils and examined to verify the one-cell stage of development for efficient gene transfer. The one-cell embryos were placed within a watch-glass filled with 1‰ (parts per thousand salinity) seawater to better visualize the penetration of the injection needle and to reduce the incidence of fungal infection. Fundulus eggs were stripped from the females immediately prior to injection, placed in a watch glass and fertilized with sperm collected by applying pressure to the abdomen of fertile males.

Injections were performed with the aid of a dissection microscope, micromanipulators, and an $N_2$ pressurized gas injection apparatus (PLI100 Medical Systems Corp., Greenvale, N.Y.). The embryos were held in place with a capillary pipette (25 μm) secured by a micromanipulator. Another capillary pipette pulled to a fine tip (1–2 μm), secured by a micromanipulator, and attached to a gas injection apparatus served as the injection needle. The DNA solution was injected through a continuously flowing pipette into the cytoplasm of the one-cell embryo, or through the micropyle when visible. This is in acontrast to the technique used in rodents, wherein the DNA solution can be directly injected into the rodent cell nucleus. It is believed that injection through the micropyle is preferable since introduction into the cytoplasm may increase the likelihood of degradation of the DNA construct and, more important, may give rise to mosaic (or chimeric) integration of the gene in the tissues of a resultant transgenic fish. That is, not all of the cells will have the heterologous DNA integrated chromosomally. Mosaic integration of the transgene in transgenic fishes is very common and is problematic because germ-line transmission is not guaranteed even if DNA extracted from a fin clip (the typical assay for integration) indicates the founder fish carries the gene. The flow rate and the total amount of solution injected was controlled by adjusting the pressure of the gas and the duration of the injection to permit injection of approximately 5–20 nl DNA solution. Medaka embryos were transferred to 20 mm petri dishes and incubated at 26° C. in sterile culture water until hatching in approximately 10 days. Fundulus embryos were placed on blotting pads on petri dishes moistened with seawater for about 14 days until hatching.

Analyses of Presumptive Transgenic Fish

Fifteen founders were obtained from the 139 medaka tested (11%), and seven out of the 15 exhibited germline transmission (47%). In the Fundulus, out of 116 fish tested, 25 were positive (22%). Thirteen of the 25 fish were tested for gerrnline transmission, and 3 of the 13 showed positive germline transmission (23%). Of the three Fundulus showing germiline transmission, one exhibited 9% transmission to its offspring, another exhibited had 11% transmission, and the third exhibited 41% transmission.

Fish tissues appear to pose a significant problem related to efficient recovery of bacteriophage and plasmid-based vectors for mutation detection. The extraction of high quality and high molecular weight genomic DNA is very important to the efficient recovery of the shuttle vector from transgenic rodent tissues. However, repeated attempts to recover shuttle vectors from transgenic fish tissues using the procedures developed for rodents have in the past been unsuccessful. Accordingly, genomic DNAs were isolated from fish tissues as generally described in R. N. Wirn et al. (*Marine Environ. Res.* 40(3):247–265 (1995)) with modifications as described herein.

Transgenic fish that demonstrated stable germ-line transmission were selected for the analysis of recovery and spontaneous mutation frequency of the plasmid shuttle vector. In addition, standard procedures for isolating genomic DNA from rodents were altered so as to insure isolation of high quality genomic DNA sufficient for recovering shuttle vectors from the fish, as described below. Specifically, transgenic $F_1$ generation fish (4–6 weeks old) were disaggregated with a dounce homogenizer containing douncing buffer (1×SSC, 1% SDS), digested with proteinase K (GibcoBRL) (37° C.) for about 1½ hours, twice extracted with equal volumes of phenol/chloroform, followed by chloroform, and precipitated with 2 volumes 100% ethanol. Precipitated DNA was spooled with a flame-sealed Pasteur Pipette, dried in air, and resuspended in 50–100 μL TE buffer (Tris 10 mM, EDTA, 1 mM, pH 7.5). Importantly, this protocol incorporates a shorter digestion time (typically about 1½ hours; sometimes up to about 2½ hours) at a lower temperature (37° C.) compared to the standard procedure used to isolate genomic DNA from mice (wherein the digestion is carried out at 50° C. for 3 hours), thus enhancing the recovery of assayable genomic DNA from the fish.

It should be noted that this DNA extraction method can be used to recover DNA directly from an organ or a tissue of a fish. The protocol is typically carried out using reduced volumes (since the amount of biological material to be extracted is reduced), and the ethanol-precipitated DNA can be isolated by centrifugation rather than by spooling. This method offers great benefit in that it allows for the study of tissue-specific mutation frequencies.

Screening for genomic integration of the pUR288 in the fish was performed by using polymerase chain reaction (PCR) methods. Amplified products (approximately 200–800 kb) were generated using several lacZ primers. The standard amplification temperature profile were as follows: denaturing 95° C., 30 seconds; annealing 60° C., 30 seconds; extending 72° C., 60 seconds. Electrophoresis of the products on an agarose gel was used to confirm amplification of the DNA fragment of appropriate size.

The zygosity of transgenic F2 generation fish was determined using quantitative PCR methods followed by verification using standard PCR analysis of DNA obtained from the offspring produced from breeding with wild-type fish in which the transmission of the plasmid to ~100% of the offspring confirmed homozygous parentage while a transmission frequency of ~50% demonstrated a hemizygous parent.

The methods for the quantitative PCR using the TaqMan system (Applied Biosystems, Calif.) entailed preparing the genomic DNA from transgenic fish in replicate at three concentrations (10 ng, 100 ng, 1000 ng). No amplification and no template DNA samples were prepared either with DNA from non-transgenic fish, or with sterile water in the place of DNA in the reagent mixture. Serial dilutions (10 ng, 100 ng, 1 ug) of genomic DNA from hemizygous and homozygous transgenic fish were used-to generate a standard curve. The forward and reverse primers consisted of a 19 mer oligonucleotide (5'-CCGCTGATCCTTTGCGAAT-3') (SEQ ID NO:1) and a 18 mer oligonucleotide (5'-CGAAGCCGCCCTGTAAAC-3') (SEQ ID NO:2), respectively, that annealed within the lacZ gene sequence to generate a PCR product. The probe that annealed within the PCR product consisted of a 31 mer oligonucleotide (5'-TGCCAGTATTTAGCGAAACCGCCAAGACTGT-3') (SEQ ID NO:3) with FAM (6-carboxy-fluorescein) as the reporter dye linked to the at 5' end, and TAMRA (6-carboxy-tetramethylrhodamine) as the quencher dye attached at the 3' end. The amplification conditions were as follows: 100 ng transgenic fish genomic DNA; 4 mM $MgSO_4$; 200 M dATP, dCTP, dGTP; 400 uM dUTP; 125 M probe; 0.625 U Amplitaq Gold™ M polymerase; 0.25 U Amerase UNG; and 1× of supplied buffer (Perkin Elmer Cetus). Using a two stage amplification profile, stage I consisted of an initial incubation of 2 minutes at 50° C., 10 minutes at 95° C.; followed by stage II with 15 seconds at 95° C., 1 minute at 60° C. for 30 cycles. A hold cycle at 25° C. was used following completion of amplification.

Example II

Determination of Spontaneous Mutation Freguency in the Target Gene

Plasmid rescue and mutation frequency analysis involved the preparation of the magnetic beads, isolation of the plasmid DNA from fish genomic DNA, electroporation of the plasmid into *E. coli*, and mutation frequency quantitation on selective plates.

The methods for preparation of the LacI repressor protein magnetic beads essentially followed previously described protocols (Gossen et al., *BioTechniques* 14, 624–629 (1993)); J. Gossen et al., *Mut. Res.* 331:89–97 (1995); see also M. Boerrigter, *Env. Mol. Mutagenesis* 32, 148–154 (1998); M. Boerrigter et al., *Nature* 377:657–659 (1995); M. Dollé et al., *Mutagenesis* 11:111–118 (1996); Boerrigter et al., *Environ. Mol. Mutagen.* 29:221–229 (1997) for additional experimental details and variations of the procedure). One mL Dynal M450 magnetic beads (Dynal AS, Oslo, Norway) coated with sheep anti-mouse IgG ($4×10^8$ magnetic beads/mL), were added to 130 μl anti-β-galactosidase (2.3 mg/mL) and incubated 45 minutes at room temperature. The magnetic beads were pelleted on a magnetic stand (Dynal) and the supernatant removed. The beads were washed 3 times for 5 minutes in 1 mL phosphate-buffered saline (PBS)/0.1% bovine serum albumin (BSA). After the last wash, the pellet was resuspended in 900 μl PBS/0.1% BSA, and 75 μl β-galactosidase/LacI repressor fiusion protein (2.0 mg/mL, Promega) was added and incubated for 2 hours at room temperature. The β-galactosidase/LacI repressor fusion protein is also commercially available from Dynal (Oslo, Norway) and Leven (Bogart, Ga.). Beads were pelleted and washed 2 times with 1 volume PBS buffer and once with storage buffer (20 mM Tris-HCl, pH 7.6, 2 mM EDTA, 5% glycerol, 1 mg/mL acetylated BSA, 0.02% Na-azide). Beads were resuspended in 1 mL storage buffer and stored at 4° C. until needed.

Transgenic fish genomic DNAs were digested with the restriction enzyme HindIII then diluted. The final recovery of about 10–50 μg fish DNA. Restriction digest of a non-mutated plasmid generates an approximately 5.5 kb fragment containing the complete pUR288 plasmid. The DNAs were added to LacI repressor magnetic beads and incubated for 1.5 hour at room temperature. Beads were washed twice with Tris-HCl, pH 7.6, 2 mM EDTA, 5% glycerol, resuspended in IPTG elution buffer (10 mM Tris-HCl, pH 7.6, 2 mM EDTA, 20 mM NaCl, 135 μg/mL IPTG) and incubated for 20 minute. The linear pUR288 DNA was circularized using T4 DNA ligase (GibcoBRL, in GibcoBRL T4 ligase buffer, which includes adenosine triphosphate [ATP] at a concentration of 0.1 mM) in a 2 hour incubation at 16° C., precipitated with 5 μg glycogen, ⅒ volume 3 M sodium acetate, pH 4.9 and 2.5 volumes cold 100% ethanol and resuspended in TE buffer.

In other experiments, the magnetic beads were prepared as described in M. Dollé et al. (*Mutagenesis* 11, 111–118 (1996); also V g et al., *Technologies for Detection of DNA Damage and Mutations*, Plenum Press, N.Y. (1996)), and the modified plasmid rescue protocol as described therein was used.

Briefly, the above protocol is streamlined by combining the HindIII digestion and the incubation with the fusion protein-coated magnetic beads simultaneously, using as a binding/excision buffer containing 10 mM Tris-HCl, 1 mM EDTA; 10 mM $MgCl_2$, 5% glycerol, pH 6.8, which also included the HindIII; a preferred binding excision buffer contains $Mg^{2+}$ from about 6–12 mM, and is about pH 6.5–7.5. IPTG elution was followed by a second HindIII digestion and the ligation, which were all done in the presence of the beads in the same tube.

Electroporation of plasmids was performed by adding circularized plasmid (1–2 μl) to electrocompetent *E. coli* C lacZ⁻, galE⁻ host cells, then electroporating at 25 μF. and 2.5 kV, 200 Ω using 0.2 cm cuvettes. After electroporation, SOC medium (2% Bacto tryptone, 0.5% Bacto yeast extract, 10 mM NaCl, 2.5 mM KCl, 10 mM $MgCl_2$, 10 mM $MgSO_4$, 20 mM glucose) was added. The cells were incubated in a shaking water bath (225 rpm) for 1 hour at 37° C. This strain is host-restriction negative, which prevents degradation of methylated plasmid DNA. The mutation in gale facilitates the selection of lacZ mutants on a medium containing lactose or a lactose-analogue such as phenyl-β-D-galactoside (βgal). GalE mutants lyse in the presence of galactose because, lacking the enzyme UDPgal 4-epimerase, they accumulate toxic amounts of UDP-galactose. Thus nonmutant host cells, which produce high β-galactosidase levels and hence convert p-gal to galactose, cannot grow, whereas the mutant host cells produce little or no β-galactosidase and thus form colonies.

Rescue efficiencies and mutation frequencies were determined substantially as described in M. Boerrigter (*Env. Mol. Mutagenesis* 32, 148–154 (1998)). Single mutant CFUs were transferred to the wells of a 96 well round bottom polystyrene cell culture plate (CoStar, Cambridge, Mass.) containing 100 μL LB medium supplemented with 75 μg/mL ampicillin and 25 μg/mL kanamycin (Sigma Chemical Co., St. Louis, Mo.) and grown for 3 hours at 37° C. To determine the sensitivity for p-gal and β-galactosidase activity, respectively, 2 μL of each cell culture was transferred to LB-agar plates, containing 75 μg/mL ampicillin, 25 μg/mL kanamycin, and either 0.3% p-gal (Sigma Chemical Co., St. Louis, Mo.) or 75 μg/mL 5-bromo-4-chloro-3-indoyl β-D-galactoside (X-gal; Promega, Madison, Wis.).

Mutant frequencies were determined as the ratio between the number of colonies on selective (p-gal) plates versus the number of colonies on non-selective (X-gal) plates, times the dilution factor. A minimum of 200,000 cfu were analyzed in each assay. Variations of the assay protocols can be found in M. Dolle et al. (*Mutagenresis* 11, 111–118 (1996)), and M. Boerrigter et al. (*Nature* 377, 657–659 (1995)). Plasmid recovery and spontaneous mutation frequency for the seven gemiline founders are set forth in Table I:

TABLE I

Plasmid recovery and spontaneous mutation frequency in medaka

| Germline Transmitting Founders | Transmission Rate | Recovery | Mutation Frequency |
|---|---|---|---|
| #9* | 16% | $5.82 \times 10^5$ | $112 \times 10^{-5}$ |
| #25 | 3% | n/a | |
| #47 | 6% | n/a | |
| #54* | 10% | n/a | n/a |
| #68* | 38% | $12 \times 10^5$ | $24 \times 10^{-5}$ |
| #127* | 44% | $40 \times 10^5$ | $9.6 \times 10^{-5}$ |
| #130 | n/a | n/a | |

*Producing F2s

Some transformed cells showed blue colors of varying intensity on the X-gal plates, suggesting that some of the mutants retained some β-galactosidase activity. Boerrigter has reported (Env. Mol. Mutagenesis 32, 148–154 (1998)) that about 21% of mutant CFUs displayed a discernable β-galactosidase activity that was less than that exhibited by nonmutant CFUs. It was found that residual β-galactosidase activity correlated with single base pair substitutions in the lacZ gene. Thus, this positive selection system has the capacity to detect a broad range of mutations, ranging from large size changes, including deletion and additions, that inactive lacZ completely to single base pair changes that only partially inactivate the lacZ gene.

Example III

Mutation Analysis

Mutants can be screened or analyzed using any suitable technique known in the art. Preliminary screening can be accomplished, for example, by assaying mutants for residual β-galactosidase activity (Example II; M. Boerrigter, *Env. Mol. Mutagenesis* 32, 148–154 (1998)), which is indicative of mutations that produce a partially gene product (e.g., single base pair mutations). Mutants can also be subjected to thermal gradient gel electrophoresis, a 2D gel electrophoresis technique that is useful in distinguishing plasmid size changes (deletions, insertions) from point mutations. By providing information about the nature of the mutation, preliminary screening techniques can make subsequent sequence analysis of a selected mutant more efficient by narrowing down the number of primers needed to successfully amplify the mutated region of the target lacZ gene.

Selected mutations can analyzed by sequence analyses of the lacZ target gene using linear amplification sequencing in which the components of a chain-termination sequencing reaction are cycled through a standard PCR temperature profile. The mutation target (lacZ) is large, thus a suite of primers is typically used to generate amplification products of a convenient size for sequencing. The lacZ template DNA are prepared for sequencing by PCR using the mutant plasmid directly as the template or by further purification. The sequencing reaction mixture (template DNA, lacZ primers, sequencing buffer, radioactive label, polymerase, water and DMSO) is cycled through a temperature profile of denaturation 95° C. 5 minutes, annealing 60° C., 30 seconds; and extension 72° C., 60 seconds. The products (2–4 μl) are loaded on a standard sequencing gel and analyzed for sequence differences. Comparisons are made of the type, number and percentages of mutations.

Mutation analysis is useful to determine the mutation spectrum characteristic of a particular mutagen, or a particular tissue, or of the action of a particular mutagen on a particular tissue.

Example IV

Mutagen Exposure Experiments

Radiation

Transgenic fish are exposed to a mutagen using a generalized exposure regimen adapted from a protocol used previously with transgenic mice carrying the plasmid vector pUR288 as the mutation target (J. Gossen et al., Mut. Res. 331, 89–97 (1995)). Radiation exposure experiments can be performed on the fish at the University of Georgia's Center for Applied Isotope Studies using an in-house $^{60}$Co irradiation source (Atomic Energy of Canada, Ltd., Gammacell 200; having a total activity of $1.22 \times 10^{13}$ Bq). To assess the effects of exposure to X-rays, X-ray treatment will be performed by whole body irradiation using a University of Georgia X-ray source.

Chemical Mutagens

N-ethyl-N-nitrosourea (ENU) is a well-characterized mutagen and carcinogen that acts by direct ethylation of oxygen and nitrogen in the bases of DNA (B. Singer, *Nature* 264:333–339 (1976)); B. Singer et al., *Nature* 276:85–88 (1978)). ENU is a useful agent for the study of the relationship of mutation to DNA repair, replication, adduct persistence, and cell differentiation (J G. Burkhart et al., *Mutation Res*. 292:69–81 (1993)). A limited study of ENU-induced mutation has been previously performed using medaka (A. Shimada et al., *Zoological Sci.* (Tokyo) 8(6): 1127 (1991); A. Shimada et al., *Zoological Sci.* (*Tokyo*) 7(6):1053 (1990)).

Dimethylnitrosamine (DMN) is a methylating agent and potent liver carcinogen in mice (International Agency for Research on Cancer (IARC), IARC Monographs on the Evaluation of the Carcinogenic Risk of Chemicals to Humans, Vol. 7, IARC, Lyon. 253p (1974)). Since cell proliferation is an important parameter for the induction of mutations, it is important to consider the influence of fixation time of adducts on the induction of mutations. DMN has been used as a representative mutagen which forms methylated DNA adducts in transgenic mice (J. C. Mirsalis et al., *Mutagenesis* 8:265–271 (1993)). DMN is among the nitrosamines that have induced hepatocarcinogenesis in fish with progressive stages similes to those characterized in rodent hepatic neoplasia (W. E. Hawkins et al., Chapter 14 in G. M. Rand, ed., Fundamentals of Aquatic Toxicology: Effects, Environmental Fate, and Risk Assessment, Taylor and Francis. 421–446 (1995)).

Exemplary Exposure Regimen

Fish mutagen exposure is performed by using protocols employed in previous transgenic rodent studies (e.g., M. J. Dycaico et al., *Mutation Res*. 307:461–478 (1994); B. J.

Rogers et al., *Mutation Res.* 327:57–66 (1995)). Specifically, one regimen consists of a single-pulse 1 to 4 hour exposure; another consists of a multiple-pulse exposure regimen consisting of 2 pulses for a 4 hour exposure for 7 days. Prior to final exposure, range-finding assays for each of the two model compounds are conducted wherein fish are exposed in single-pulse and multiple-pulse treatments over a range of mutagen concentrations to determine the upper exposure concentration expected to produce minimal or zero lethality (about 50% of the lowest exposure concentration at which deaths occur). The range finding trials in the present example are 0, 25, 50 and 100 ppm of ENU or DMN. In previous mutagen exposure studies using λLIZ transgenic fish, doses of about 0.5 mM (60 ppm) of ENU ($LD_{50}$ ~350 mg/kg) were used to obtain a two-fold mutation frequency induction, and doses of about 120 ppm of ENU were used to obtain four-fold mutation frequency induction in medaka.

Fish are placed in replicate 50 mL glass test chambers (10/chamber). The mutagen solutions, at concentrations determined by dilution factors, are added to water immediately prior to the initiation of exposure. Toxicant-free treatments accompany all exposures as controls. For the multiple-pulse regimen, fish are transferred and held in clean water to await the next exposure. The fish are not fed during the exposure period. During the exposure phase, fish are monitored regularly for any visual signs of distress. Any dead or moribund fish are removed.

Following the final exposure series, fish are rinsed and transferred to grow-out aquaria for a prescribed expression time. During this time fish are held in aquaria in toxicant-free water at 26° C. on a 12:12 hour light:dark regime and fed twice daily. The fish are visually monitored at least twice daily during feeding. Any fish that have died, or that exhibit abnormal swimming behaviors or other visible signs of distress, are removed from the aquaria. Fish that show apparent formation of external neoplasms are removed, sacrificed, and saved for furthers analyses, if desired.

The influence of expression time on the mutation frequency is evaluated by sampling fish at 5, 10, 15 and 30 days following exposure. Expression time, or fixation time, is defined as the time allowed between dosing and sacrificing the animals for mutation assays. Some expression time is required, especially after single-dose administrations, to permit uptake and distribution of the chemical, metabolic activation to a DNA-reactive form, formation of adducts, and at least one cell division to "fix" the adduct as a heritable mutation. Although there is no data currently available on mutations rates, DNA repair, or cell proliferation in transgenic medaka, it is believed that a long expression time (>7 days) would allow adequate time to either repair DNA adducts or fix adducts as mutations. This reduces the possibility the DNA adducts will be mutated by the host *E. coli* by decreasing the number of DNA adducts present on the recovered target DNA.

Upon termination of the expression phase, fish are euthanized by overdose of MS-222 (tricaine methanesulfonate). Selected tissues are dissected and flash frozen in liquid nitrogen and stored at −70° C. Genomic DNA is isolated, the heterologous nucleic acid sequence is rescued, and mutation frequency is analyzed as in Example II.

The complete disclosures of all patents, patent applications, publications, database entries, submissions and deposits, including GENBANK deposits and the descriptive information associated therewith, and other documents cited herein are fully incorporated herein in their entireties by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for detecting mutations in the DNA of a transenic fish comprising:
   providing a transgenic fish, wherein the DNA of the transgenic fish comprises multiple concatemeric genomically integrated copies of a plasmid comprising an assayable mutation target nucleic acid sequence;
   gently disaggregating at least a portion of the fish to yield disaggregated fish material;
   digesting the disaggregated fish material with a proteinase for a period of no longer than about 1-½ hours at a temperature of about 37° C.;
   extracting DNA comprising the mutation target nucleic acid sequence from the disaggregated fish material sufficient to detect a mutation in the mutation target nucleic acid sequence; and
   detecting the presence of a mutation in the mutation target nucleic acid sequence.

2. The method of claim 1 wherein the extracting step yields extracted DNA comprising plasmid DNA and chromosomal DNA.

3. The method of claim 2 further comprising cleaving the extracted DNA with a restriction endonuclease to yield at least one DNA fragment comprising the plasmid-derived mutation target nucleic acid sequence and a multiplicity of DNA fragments comprising chromosomal DNA.

4. The method of claim 3 further comprising separating the DNA fragment comprising the plasmid-derived mutation target nucleic acid sequence from the multiplicity of DNA fragments comprising chromosomal DNA to yield isolated plasmid-derived DNA comprising the mutation target nucleic acid sequence.

5. The method of claim 4 wherein the assayable mutation target nucleic acid sequence comprises a lacZ gene comprising a lacZ operator.

6. The method of claim 5 wherein the step of separating the DNA fragment comprising the plasmid-derived mutation target nucleic acid sequence from the multiplicity of DNA fragments comprising chromosomal DNA comprises:
   contacting the DNA fragments with an affinity support comprising a lacZ operator binding material to bind the DNA fragment comprising the plasmid-derived mutation target nucleic acid sequence; and
   eluting the bound DNA fragment from the support.

7. The method of claim 6 wherein the contacting step is performed after the cleaving step.

8. The method of claim 1 wherein the providing step comprises providing a transgenic fish that has been or is suspected of having been exposed to a mutagen.

9. The method of claim 6 wherein the contacting step and the cleaving step are performed simultaneously.

10. The method of claim 1 further comprising exposing the transgenic fish to a mutagen prior to extracting the DNA comprising the mutation target nucleic acid sequence.

11. The method of claim 10 wherein the mutagen is selected from the group consisting of a chemical, a radioisotope and electromagnetic radiation.

12. The method of claim 1 wherein the DNA is extracted from an organ or tissue of the transgenic fish.

13. The method of claim 12 further comprising analyzing the mutation.

14. The method of claim 13 wherein the step of analyzing the mutation comprises determining a tissue-specific or organ specific mutation frequency.

15. The method of claim 1 wherein the fish is selected from the group consisting of a medaka and a fundulus.

16. The method of claim 1 wherein the assayable mutation target nucleic acid sequence comprises a lacZ gene comprising a lacZ operator.

17. The method of claim 16 wherein the step of detecting the presence of a mutation in the mutation target nucleic acid sequence comprises:
   transforming a host restriction-negative, lacZ⁻galE⁻ bacterial host with the recovered DNA comprising the lacZ gene;
   culturing the transformed bacterial host on a lactose-containing or lactose analogue-containing medium; and
   selectively detecting a transformed bacterial host that comprises a mutation in the lacZ gene, wherein growth of the bacterial host is indicative of the existence of said mutation.

18. The method of claim 17 comprising, prior to transforming the bacterial host, ligating the recovered DNA to yield a circular DNA.

19. The method of claim 1 wherein the assayable mutation target nucleic acid sequence comprises a nucleic acid sequence selected from the group consisting of a lacI gene sequence, a lacZ gene sequence and a lac promoter sequence.

20. The method of claim 1 wherein the step of detecting the presence of a mutation in the mutation target nucleic acid sequence comprises performing a bioassay.

21. The method of claim 1 further comprising analyzing the mutation in the mutation target nucleic acid sequence.

22. The method of claim 21 wherein the step of analyzing the mutation comprises determining the nucleic acid sequence of at least a portion of the mutation target nucleic acid sequence.

23. A method for evaluating the mutagenicity of a suspected mutagen comprising:
   exposing a transgenic fish to a suspected mutagen, wherein the DNA of the transgenic fish comprises multiple concatemeric genomically integrate copies of a plasmid comprising an assayable mutation target nucleic acid sequence;
   gently disaggregating at least a portion of the fish to yield disaggregated fish material;

digesting the disaggregated fish material with a proteinase for a period of no longer than about 1-½ hours at a temperature of about 37° C.;

extracting DNA comprising the mutation target nucleic acid sequence from the disaggregated fish material sufficient to detect a mutation in the mutation target nucleic acid sequence; and detecting the presence of a mutation in the mutation target nucleic acid sequence.

24. The method of wherein 23 wherein the DNA is extracted from an organ or tissue of the transgenic fish.

25. The method of claim 24 furthers comprising analyzing the mutation.

26. The method of claim 25 wherein the step of analyzing the mutation comprises determining a tissue-specific or organ specific mutation frequency.

27. The method of claim 23 wherein the fish is selected from the group consisting of a medaka and a fundulus.

28. The method of claim 23 wherein the assayable mutation target nucleic acid sequence comprises a nucleic acid sequence selected from the group consisting of a lacI gene sequence, a lacZ gene sequence and a lac promoter sequence.

29. The method of claim 23 further comprising analyzing the mutation in the mutation target nucleic acid sequence.

30. The method of claim 29 wherein the step of analyzing the mutation comprises determining the nucleic acid sequence of at least a portion of the mutation target nucleic acid sequence.

31. The method of claim 29 wherein analyzing the mutation comprises determining a mutation spectrum of the suspected mutagen.

32. The method of claim 23 wherein the assayable mutation target nucleic acid sequence comprises a lacZ gene comprising a lacZ operator.

* * * * *

UNITED STATES PATENT AND TRADEMARK OFFICE
CERTIFICATE OF CORRECTION

PATENT NO. : 6,472,583 B1  Page 1 of 1
APPLICATION NO. : 09/427218
DATED : October 29, 2002
INVENTOR(S) : Richard N. Winn It is certified that error appears in the above-identified patent and that said Letters Patent is hereby corrected as shown below:

Insert the following statement prior to the paragraph entitled FIELD OF THE INVENTION beginning at column 1, line 6:

--STATEMENT OF GOVERNMENT RIGHTS

This invention was made with government support under Grant No. R24RR11733 awarded by the National Center for Research Resources, National Institutes of Health. The government has certain rights in the invention.--

Signed and Sealed this

Eleventh Day of November, 2008

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 1
ccgctgatcc tttgcgaat                                                19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 2
cgaagccgcc ctgtaaac                                                 18

<210> SEQ ID NO 3
```

-continued

```
<211> LENGTH: 31
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 3
tgccagtatt tagcgaaacc gccaagactg t                                   31
```